(12) United States Patent
Ferro et al.

(10) Patent No.: US 7,476,744 B2
(45) Date of Patent: Jan. 13, 2009

(54) POLYMORPHIC CRYSTALLINE FORMS OF CELECOXIB

(75) Inventors: Leonard J. Ferro, Highland Park, IL (US); Patricia S. Miyake, Tower Lakes, IL (US)

(73) Assignee: Pfizer Inc., New York, NY (US)

( * ) Notice: Subject to any disclaimer, the term of this patent is extended or adjusted under 35 U.S.C. 154(b) by 297 days.

(21) Appl. No.: 09/728,040

(22) Filed: Dec. 1, 2000

(65) Prior Publication Data

US 2004/0087640 A1    May 6, 2004

Related U.S. Application Data

(60) Provisional application No. 60/169,856, filed on Dec. 9, 1999.

(51) Int. Cl.
C07D 231/00    (2006.01)

(52) U.S. Cl. .................................................. 548/375.1

(58) Field of Classification Search ................. 514/406; 548/377.1, 375.1
See application file for complete search history.

(56) References Cited

U.S. PATENT DOCUMENTS

| | | | |
|---|---|---|---|
| 4,826,689 A | 5/1989 | Violanto | 424/489 |
| 5,145,684 A | 9/1992 | Liversidge et al. | 424/489 |
| 5,298,262 A | 3/1994 | Na et al. | 424/489 |
| 5,302,401 A | 4/1994 | Liversidge et al. | 424/501 |
| 5,336,507 A | 8/1994 | Na et al. | 424/489 |
| 5,340,564 A | 8/1994 | Illig et al. | 424/9 |
| 5,346,702 A | 9/1994 | Na et al. | 424/490 |
| 5,352,459 A | 10/1994 | Hollister et al. | 424/489 |
| 5,354,560 A | 10/1994 | Loverich | 424/489 |
| 5,384,124 A | 1/1995 | Courteille et al. | 424/430 |
| 5,429,824 A | 7/1995 | June | 424/489 |
| 5,466,823 A * | 11/1995 | Talley et al. | 548/377.1 |
| 5,474,995 A | 12/1995 | Ducharme et al. | 514/241 |
| 5,503,723 A | 4/1996 | Ruddy et al. | 204/450 |
| 5,510,118 A | 4/1996 | Bosch et al. | 424/489 |
| 5,518,738 A | 5/1996 | Eickhoff et al. | 424/493 |
| 5,534,270 A | 7/1996 | De Castro | 424/490 |
| 5,536,508 A | 7/1996 | Canal et al. | 424/501 |
| 5,552,160 A | 9/1996 | Liversidge et al. | 424/489 |
| 5,560,931 A | 10/1996 | Eickhoff et al. | 424/489 |
| 5,560,932 A | 10/1996 | Bagchi et al. | 424/489 |
| 5,565,188 A | 10/1996 | Wong et al. | 424/9.411 |
| 5,569,448 A | 10/1996 | Wong et al. | 424/9.45 |
| 5,571,536 A | 11/1996 | Eickhoff et al. | 424/489 |
| 5,573,783 A | 11/1996 | Desieno et al. | 424/490 |
| 5,580,579 A | 12/1996 | Ruddy et al. | 424/489 |
| 5,585,108 A | 12/1996 | Ruddy et al. | 424/434 |
| 5,587,143 A | 12/1996 | Wong | 424/9.1 |
| 5,591,456 A | 1/1997 | Franson et al. | 424/494 |
| 5,633,272 A | 5/1997 | Talley et al. | 514/378 |
| 5,662,883 A | 9/1997 | Bagchi et al. | 424/9.4 |
| 5,665,331 A | 9/1997 | Bagchi et al. | 424/9.45 |
| 5,718,919 A | 2/1998 | Ruddy et al. | 424/489 |
| 5,747,001 A | 5/1998 | Wiedmann et al. | 424/45 |
| 5,760,068 A | 6/1998 | Talley et al. | 514/403 |
| 5,981,576 A | 11/1999 | Belley et al. | 514/473 |
| 2002/0006951 A1 * | 1/2002 | Hageman et al. | 514/406 |

FOREIGN PATENT DOCUMENTS

| | | |
|---|---|---|
| EP | 0863134 | 9/1998 |
| WO | 93/25190 | 12/1993 |
| WO | 96/24336 | 8/1996 |
| WO | 98/35666 | 8/1998 |
| WO | 99/55380 | 11/1999 |

OTHER PUBLICATIONS

Nicholas D. Cheronis, 1958, "Semicro Experimental Organic Chemistry", Chapter 5.*
Brittain, polymorphism in Pharmaceutical Solids, Drugs and the Pharmaceutical Science; 1999, V. 95, pp. 348-361.*
John Vane; Nature News & Perspectives; vol. 7; 501-512; 1994.

* cited by examiner

*Primary Examiner*—Rei-tsang Shiao
(74) *Attorney, Agent, or Firm*—Gregg C. Benson; Rona A. Nardone

(57) ABSTRACT

Pharmaceutical compositions are provided comprising one or more orally deliverable dose units, each comprising a selective cyclooxygenase-2 inhibitory compound of low water solubility in a therapeutically effective amount, wherein the compound is present in the form of solid particles, about 25% to 100% by weight of which are smaller than 1 micrometer. The compositions are useful in treatment or prophylaxis of cyclooxygenase-2 mediated conditions and disorders and have particular advantages where rapid onset of therapeutic effect is desired. The novel Form I and Form II crystalline forms of celecoxib are described. The crystalline forms have unique chemical and physical properties relative to other solid state forms of celecoxib and are characterized by their powder x-ray diffraction (PXRD) patterns, differential scanning calorimetric (DSC) thermograms, and other physical characterizations.

19 Claims, 3 Drawing Sheets

POLYMORPHIC CRYSTALLINE FORMS OF CELECOXIB

CROSS REFERENCE TO RELATED APPLICATIONS

This Patent Application claims priority to U.S. Provisional Patent Application Ser. No. 60/169,856, filed Dec. 9, 1999.

FIELD OF THE INVENTION

The present invention relates to orally deliverable pharmaceutical compositions containing a cyclooxygenase-2 inhibitory drug as an active ingredient, to processes for preparing such compositions, to methods of treatment of cyclooxygenase-2 mediated disorders comprising orally administering such compositions to a subject, and to the use of such compositions in the manufacture of medicaments.

This invention is in the field of cyclooxygenase-2 inhibitory pharmaceutical agents and specifically relates to the novel Form I and Form II crystalline forms of celecoxib, methods of preparing these crystalline forms of celecoxib, pharmaceutical compositions comprising these crystalline forms of celecoxib, and methods for the treatment and/or prophylaxis of cyclooxygenase-2-mediated conditions and/or disorders, including conditions and disorders.

BACKGROUND OF THE INVENTION

Numerous compounds have been reported having therapeutically and/or prophylactically useful selective cyclooxygenase-2 inhibitory effect, and have been disclosed as having utility in treatment or prevention of specific cyclooxygenase-2 mediated disorders or of such disorders in general. Among such compounds are a large number of substituted pyrazolyl benzenesulfonamides as reported in U.S. Pat. No. 5,760,068 to Talley et al., including for example the compound 4-[5-(4-methylphenyl)-3-(trifluoromethyl)-1H-pyrazol-1-yl]benzenesulfonamide, also referred to herein as celecoxib, and the compound 4-[5-(3-fluoro-4methoxyphenyl)-3-difluoromethyl)-1H-pyrazol-1-yl]benzenesulfonamide, also referred to herein as deracoxib. Celecoxib has the structure:

(I)

and deracoxib has the structure:

(II)

Other compounds reported to have therapeutically and/or prophylactically useful selective cyclooxygenase-2 inhibitory effect are substituted isoxazolyl benzenesulfonamides as reported in U.S. Pat. No. 5,633,272 to Talley et al., including for example the compound 4-[5-methyl-3-phenylisoxazol-4-yl]benzenesulfonamide, also referred to herein as valdecoxib, which has the structure:

(III)

Still other compounds reported to have therapeutically and/or prophylactically useful selective cyclooxygenase-2 inhibitory effect are substituted (methylsulfonyl)phenyl furanones as reported in U.S. Pat. No. 5,474,995 to Ducharme et al., including for example the compound 3-phenyl-4-[4-(methylsulfonyl)phenyl]-5H-furan-2-one, also referred to herein as rofecoxib, which has the structure:

(IV)

U.S. Pat. No. 5,981,576 to Belley et al. discloses a further series of (methylsulfonyl)phenyl furanones said to be useful as cyclooxygenase-2-inhibitors, including 3-(1-cyclopropylmethoxy)-5,5dimethyl-4-[4-(methylsulfonyl)phenyl]-5H-furan-2-one and 3-(1-cyclopropylethoxy)-5,5-dimethyl-4-[4-(methylsulfonyl)phenyl]-5H-furan-2-one.

European Patent Application No. 0 863 134 discloses the compound 2-(3,5-difluorophenyl)-3-[4-(methylsulfonyl)phenyl]-2-cyclopenten-1-one said to be useful as a cyclooxygenase-2 inhibitor.

International Publication No. WO 99/55380 discloses, inter alia, a compound having the structure:

(V)

said to be useful as a cyclooxygenase-2 inhibitor.

Many selective cyclooxygenase-2 inhibitory compounds, including celecoxib, deracoxib, valdecoxib and rofecoxib, are hydrophobic and have low solubility in water. This has presented practical difficulties in formulating such compounds for oral administration, particularly where early onset of therapeutic effect is desired or required.

Illustratively, the formulation of celecoxib for effective oral administration to a subject has hitherto been complicated by the unique physical and chemical properties of celecoxib, particularly its low solubility and factors associated with its crystal structure, including cohesiveness, low bulk density and low compressibility. Celecoxib is unusually insoluble in aqueous media. Unformulated celecoxib is not readily dissolved and dispersed for rapid absorption in the gastrointestinal tract when administered orally, for example in capsule form. In addition, unformulated celecoxib, which has a crystal morphology that tends to form long cohesive needles, typically fuses into a monolithic mass upon compression in a tableting die. Even when blended with other substances, the celecoxib crystals tend to separate from the other substances and agglomerate together during mixing of the composition resulting in a non-uniformly blended composition containing undesirably large aggregates of celecoxib. Therefore, it is difficult to prepare a pharmaceutical composition containing celecoxib that has the desired blend uniformity. Further, handling problems are encountered during the preparation of pharmaceutical compositions comprising celecoxib. For example, the low bulk density of celecoxib makes it difficult to process the small quantities required during formulation of the pharmaceutical compositions. Accordingly, a need exists for solutions to numerous problems associated with preparation of suitable pharmaceutical compositions and dosage forms comprising celecoxib, particularly orally deliverable dose units.

More generally, a need exists for orally deliverable formulations of cyclooxygenase-2 inhibitory drugs of low water solubility including celecoxib, such formulations possessing one or more of the following characteristics relative to unformulated celecoxib or other celecoxib compositions:

(1) improved solubility;
(2) shorter disintegration time;
(3) shorter dissolution time;
(4) decreased tablet friability;
(5) increased tablet hardness;
(6) improved wettability;
(7) improved compressibility;
(8) improved flow properties of liquid and particulate solid compositions;
(9) improved physical stability of the finished composition;
(10) reduced tablet or capsule size;
(11) improved blend uniformity;
(12) improved dose uniformity;
(13) improved control of weight variation during encapsulation and/or tableting;
(14) increased granule density for wet granulated compositions;
(15) Reduced water requirement for wet granulation;
(16) Reduced wet granulation time; and
(17) Reduced drying time for wet granulated mixtures.

Further, there exists an especial need for orally deliverable formulations of cyclooxygenase-2 inhibitory drugs of low water solubility including celecoxib, such formulations providing more rapid onset of therapeutic effect than the corresponding unformulated drugs or known formulations of these drugs. To the extent that rapid onset of therapeutic effect is related to pharmacokinetic parameters such as a high maximum blood serum concentration of the drug ($C_{max}$) and a short time from oral administration to reach such maximum blood serum concentration ($T_{max}$), there is an especial need for orally deliverable formulations of cyclooxygenase-2 inhibitory drugs of low water solubility including celecoxib, such formulations providing a greater $C_{max}$ and/or an earlier $T_{max}$ than the corresponding unformulated drugs or known formulations of these drugs.

As is indicated herein below, treatment with selective cyclooxygenase-2 inhibitors including celecoxib is indicated or potentially indicated in a very wide array of cyclooxygenase-2 mediated conditions and disorders. It would be of benefit to provide formulations exhibiting pharmacokinetics consistent with rapid onset of therapeutic effect especially for treatment of acute disorders where early relief from pain or other symptoms is desired or required.

Such formulations would represent a significant advance in the treatment of cyclooxygenase-2 mediated conditions and disorders.

Cyclooxygenase-2 inhibitory drugs including celecoxib that are of low solubility in water are most conveniently formulated in solid particulate form. The individual or primary particles of the drug can dispersed in a liquid medium, as in a suspension formulation, or can be aggregated to form secondary particles or granules that can be encapsulated to provide a capsule dosage form, or compressed or molded to provide a tablet dosage form.

Numerous processes are known and used in the art for preparing drug formulations having primary particle sizes in a desired range, or having a desired mean particle size, or having a particle size distribution characterized by a parameter such as $D_{90}$, which is defined herein as a linear measure of diameter having a value such that 90% by volume of particles in the formulation, in the longest dimension of the particles, are smaller than that diameter. For practical purposes a determination of $D_{90}$ based on 90% by weight rather than by volume is generally suitable.

For consistency with prior publications, the terms "microparticle" and "nanoparticle" are defined herein as in U.S. Pat. No. 5,384,124 to Courteille et al., to refer to particles having respectively a diameter of between 1 micrometer and 2000 micrometers and a diameter of less than 1 micrometer (1000 nm). The preparation of microparticles and nanoparticles, according to U.S. Pat. No. 5,384,124, "is principally used to retard dissolution of active principles". However, U.S. Pat. No. 5,145,684 to Liversidge et al. discloses nanoparticulate compositions said to provide "unexpectedly high bioavailability" of drugs, particularly drugs having low solubility in a liquid medium such as water. International Publication No. WO 93/25190 provides pharmacokinetic data from a rat study indicating a higher apparent rate of absorption from oral administration of a nanoparticulate (average particle size 240-300 nm) than from oral administration of a microparticulate (particle size range 20-30 micrometer) dispersion of naproxen.

Numerous processes for preparation of nanoparticulate compositions of therapeutic agents are known. Typically these processes use mechanical means, such as milling or grinding, to reduce particle size to a nano (less than 1 micrometer) range, or precipitate nano-sized particles from solution. Illustrative processes are disclosed in the following individual references: U.S. Pat. No. 4,826,689 to Violanto & Fischer, above-cited U.S. Pat. No. 5,145,684 to Liversidge et al., U.S. Pat. No. 5,298,262 to Na & Rajagopalan, U.S. Pat. No. 5,302,401 to Liversidge et al., U.S. Pat. No. 5,336,507 to Na & Rajagopalan, U.S. Pat. No. 5,340,564 to Illig & Sarpotdar, U.S. Pat. No. 5,346,702 to Na & Rajagopalan, U.S. Pat. No. 5,352,459 to Hollister et al., U.S. Pat. No. 5,354,560 to Lovrecich, above-cited U.S. Pat. No. 5,384,124 to Courteille et al., U.S. Pat. No. 5,429,824 to June, U.S. Pat. No. 5,510,118 to Bosch et al., U.S. Pat. No. 5,518,738 to Eickhoff et al., U.S.

Pat. No. 5,503,723 to Ruddy & Eickhoff, U.S. Pat. No. 5,534,270 to De Castro, U.S. Pat. No. 5,536,508 to Canal et al., U.S. Pat. No. 5,552,160 to Liversidge et al., U.S. Pat. No. 5,560,931 to Eickhoff et al., U.S. Pat. No. 5,560,932 to Bagchi et al., U.S. Pat. No. 5,565,188 to Wong et al., U.S. Pat. No. 5,569,448 to Wong et al., U.S. Pat. No. 5,571,536 to Eickhoff et al., U.S. Pat. No. 5,573,783 to Desieno & Stetsko, U.S. Pat. No. 5,580,579 to Ruddy et al., U.S. Pat. No. 5,585,108 to Ruddy et al., U.S. Pat. No. 5,587,143 to Wong, U.S. Pat. No. 5,591,456 to Franson & Snyder, U.S. Pat. No. 5,662,883 to Bagchi et al., U.S. Pat. No. 5,665,331 to Bagchi et al., U.S. Pat. No. 5,718,919 to Ruddy & Roberts, U.S. Pat. No. 5,747,001 to Wiedmann et al., International Publication No. WO 93/25190, International Publication No. WO 96/24336, International Publication No. 98/35666.

SUMMARY OF THE INVENTION

According to the present invention, a poorly water soluble selective cyclooxygenase-2 inhibitory compound such as celecoxib, deracoxib, valdecoxib or rofecoxib provides more rapid onset of therapeutic effect if, upon oral administration of a composition comprising the compound, the compound exhibits pharmacokinetic properties leading to a greater maximum blood serum concentration ($C_{max}$) and/or a shorter time following the administration to reach that maximum ($T_{max}$). It is contemplated that a greater $C_{max}$ and/or a shorter $T_{max}$ are obtained by reduction of size of solid particles comprising the compound such that a substantial portion by weight of the particles are smaller than 1 micrometer in diameter, in the longest dimension of the particles. Without being bound by theory, it is believed that the greater $C_{max}$ and/or the shorter $T_{max}$ result from faster dissolution of the compound when particle size is reduced to less than 1 micrometer.

Accordingly, there is now provided a pharmaceutical composition comprising one or more orally deliverable dose units, each comprising a selective cyclooxygenase-2 inhibitory compound of low water solubility in a therapeutically effective amount, wherein the compound is present in solid particles having a $D_{90}$ particle size of about 0.01 to about 200 micrometer, a sufficient portion by weight of the particles being smaller than 1 micrometer to provide a substantially higher $C_{max}$ and/or a substantially shorter $T_{max}$ by comparison with an otherwise similar composition wherein substantially all of the particles are larger than 1 micrometer.

There is also provided a pharmaceutical composition comprising one or more orally deliverable dose units, each comprising a selective cyclooxygenase-2 inhibitory compound of low water solubility in a therapeutically effective amount, wherein the compound is present in solid particles having a $D_{90}$ particle size of about 0.01 to about 200 micrometer, and wherein about 25% to 100% by weight of the particles are smaller than 1 micrometer.

The dose units comprising the composition can be in the form of discrete solid articles such as tablets, pills, hard or soft capsules, lozenges, sachets or pastilles; alternatively the composition can be in the form of a substantially homogeneous flowable mass, such as a particulate or granular solid or a liquid suspension, from which single dose units are measurably removable.

Also provided is a method of treating a medical condition or disorder in a subject where treatment with a cyclooxygenase-2 inhibitor is indicated, comprising orally administering one or more dose units of a composition of the invention once or twice a day. Such a method is particularly useful where the medical condition or disorder is accompanied by acute pain.

The present invention also embodies a novel solid state form of celecoxib, Form I celecoxib. The present invention further embodies another solid state form of celecoxib, Form II celecoxib. Each of these novel solid state forms includes solvated crystalline forms, non-solvated and non-hydrated crystalline forms. These novel forms of celecoxib described in the present application possess one or more of the above-described advantageous chemical and/or physical properties relative to the other solid state forms described herein or otherwise disclosed in the literature.

Another embodiment of the present invention comprises a novel crystalline form of celecoxib. For example, one embodiment of the present invention includes a Form I crystalline form of celecoxib, preferably a crystalline form having an X-ray powder diffraction pattern with peaks at 5.5, 5.7, 7.2, and 16.6 degrees two theta.

In another embodiment, the present invention provides a pharmaceutical composition comprising a therapeutically-effective amount of the Form I crystalline form of celecoxib and at least one pharmaceutically-acceptable carrier, adjuvant or diluent.

In another embodiment, the present invention provides a method of treating or preventing a cyclooxygenase-2-mediated condition or disorder in a subject, wherein the method comprises administering to the subject a therapeutically effective amount of Form I celecoxib.

In yet another embodiment, the present invention provides a method of preparing Form I celecoxib comprising crystallizing celecoxib from a mixture comprising celecoxib and a solvent, wherein the crystallization is performed at a temperature above the enantiotropic transition temperature of Form I celecoxib thereby producing Form I celecoxib.

In still another embodiment, the present invention provides a method of preparing a crystalline form of celecoxib wherein the method comprises heating a solvate of celecoxib thereby producing Form I celecoxib.

In another embodiment, the present invention provides a method of producing Form I celecoxib wherein the method comprises milling or grinding Form III celecoxib thereby producing Form I celecoxib.

In yet another embodiment, the present invention provides a method of producing Form I celecoxib wherein the method comprises milling or grinding a celecoxib solvate thereby producing Form I celecoxib.

In another embodiment, the present invention provides a method of producing Form I celecoxib wherein the method comprises melting Form II celecoxib and cooling the melt thereby producing Form I celecoxib.

In another embodiment, the present invention provides a method of producing Form I celecoxib wherein the method comprises melting Form III celecoxib and cooling the melt thereby producing Form I celecoxib.

In another embodiment, the present invention provides a method of producing Form I celecoxib wherein the method comprises evaporating solvent from a celecoxib solution thereby producing Form I celecoxib.

Another embodiment of the present invention comprises a novel crystalline form of celecoxib. For example, one embodiment of the present invention includes a Form II crystalline form of celecoxib, preferably a crystalline form having an X-ray powder diffraction pattern with a peak at about 10.3, 13.8 or 17.7 degrees two theta.

Another embodiment of the present invention provides a pharmaceutical composition comprising a therapeutically-effective amount of the crystalline form of at least one pharmaceutically-acceptable carrier, adjuvant or diluent.

Another embodiment of the present invention provides a method of treating or preventing a cyclooxygenase-2-mediated condition or disorder in a subject, the method comprising administering to the subject a therapeutically-effective amount of Form II celecoxib.

Yet another embodiment of the present invention provides a method of preparing Form II celecoxib comprising crystallizing celecoxib from a mixture comprising celecoxib and a solvent, wherein the crystallization is performed at a temperature above the enantiotropic transition temperature of Form II celecoxib thereby producing Form II celecoxib.

Yet another embodiment of the present invention provides a method of preparing a crystalline form of celecoxib wherein the method comprises heating a solvate of celecoxib thereby producing Form II celecoxib.

Another embodiment of the present invention provides a method of producing Form II celecoxib wherein the method comprises milling or grinding Form III celecoxib thereby producing Form II celecoxib.

Another embodiment of the present invention provides a method of producing Form II celecoxib wherein the method comprises milling or grinding a celecoxib solvate thereby producing Form II celecoxib.

Still another embodiment of the present invention provides a method of producing Form II celecoxib wherein the method comprises melting Form I celecoxib and cooling the melt thereby producing Form II celecoxib.

Yet another embodiment of the present invention provides a method of producing Form II celecoxib wherein the method comprises melting Form III celecoxib and cooling the melt thereby producing Form II celecoxib.

Another embodiment of the present invention provides a solid form of celecoxib comprising Form I celecoxib and Form II celecoxib.

Another embodiment of the present invention provides a solid form of celecoxib comprising Form I celecoxib and Form III celecoxib.

Another embodiment of the present invention provides a solid form of celecoxib comprising Form II celecoxib and Form III celecoxib.

Another embodiment of the present invention provides a solid form of celecoxib comprising Form I celecoxib, Form II celecoxib, and Form III celecoxib.

Other features of this invention will be in part apparent and in part pointed out hereinafter.

DESCRIPTION OF THE PREFERRED EMBODIMENTS

The term "selective cyclooxygenase-2 inhibitor" or "selective cyclooxygenase-2 inhibitory compound" herein means a compound that inhibits cyclooxygenase-2 to a therapeutically useful degree while causing markedly less inhibition of cyclooxygenase-1 than conventional nonsteroidal anti-inflammatory drugs (NSAIDs).

The term "poorly water soluble" or "of low water solubility" with respect to a selective cyclooxygenase-2 inhibitor herein means having a solubility in distilled water at 25° C lower than about 10 g/l, preferably lower than about 1 g/l.

The term "oral administration" herein includes any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. Absorption of the agent can occur in any part or parts of the gastrointestinal tract including the mouth, esophagus, stomach, duodenum, ileum and colon.

The term "orally deliverable" herein means suitable for oral administration.

A "subject" herein to which a therapeutic agent or composition thereof can be administered includes a human patient of either sex and of any age, and also includes any nonhuman animal, particularly a domestic or companion animal, illustratively a cat, dog or horse.

The term "dose unit" herein means a portion of a pharmaceutical composition that contains an amount of a therapeutic agent, in the present case a selective cyclooxygenase-2 inhibitor, suitable for a single oral administration to provide a therapeutic effect. Typically one dose unit, or a small plurality (up to about 4) of dose units, provides a sufficient amount of the agent to result in the desired effect.

The term "present in solid particles" as applied to a selective cyclooxygenase-2 inhibitory compound herein encompasses compositions wherein the solid particles consist essentially of the compound and compositions where the solid particles comprise the compound in intimate mixture with one or more other ingredients. These other ingredients can include one or more therapeutic agents other than the selective cyclooxygenase-2 inhibitory compound and/or one or more pharmaceutically acceptable excipients.

The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, lubricants, glidants, substances added to mask or counteract a disagreeable taste or odor, flavors, dyes, fragrances, and substances added to improve appearance of the composition.

The term "substantially homogeneous" with reference to a pharmaceutical composition that comprises several components means that the components are sufficiently mixed such that individual components are not present as discrete layers and do not form concentration gradients within the composition.

The term "purity" means the chemical purity of celecoxib according to conventional HPLC assay.

The term "phase purity" means the solid state purity of celecoxib with regard to a particular crystalline or amorphous form of the celecoxib as determined by the infrared spectroscopy analytical methods described herein.

The term "enantiotropic transition temperature" means the temperature at which a thermodynamically stable polymorph changes from one form to another. For example, for two polymorphs, Form A and Form B, below the enantiotropic transition temperature, Form A may be the thermodynamically stable form, but above this temperature Form B may be the thermodynamically stable form.

Novel pharmaceutical compositions according to the present invention comprise one or more orally deliverable dose units. Each dose unit comprises a selective cyclooxygenase-2 inhibitor, illustratively celecoxib, in a therapeutically effective amount that is preferably about 10 mg to about 1000 mg.

It will be understood that a therapeutically effective amount of a selective cyclooxygenase-2 inhibitor for a subject is dependent inter alia on the body weight of the subject. Where the cyclooxygenase-2 inhibitor is celecoxib and the subject is a child or a small animal (e.g., a dog), for example, an amount of celecoxib relatively low in the preferred range of about 10 mg to about 1000 mg is likely to provide blood serum concentrations consistent with therapeutic effectiveness. Where the subject is an adult human or a large animal (e.g., a horse), achievement of such blood serum concentrations of celecoxib are likely to require dose units containing a relatively greater amount of celecoxib.

Typical dose units in a composition of the invention contain about 10, 20, 25, 37.5, 50, 75, 100, 125, 150, 175, 200, 250, 300, 350 or 400 mg of the cyclooxygenase-2 inhibitor, illustratively celecoxib. For an adult human, a therapeutically effective amount of celecoxib per dose unit in a composition of the present invention is typically about 50 mg to about 400 mg. Especially preferred amounts of celecoxib per dose unit are about 100 mg to about 200 mg, for example about 100 mg or about 200 mg.

Compositions of the present invention contain a selective cyclooxygenase-2 inhibitor, illustratively celecoxib, alone or in intimate mixture with one or more excipients, in nanoparticulate form, i.e., in the form of solid particles of diameter less than 1 micrometer in the longest dimension of the particles.

The effects on pharmacokinetic properties of reducing particle size from the microparticle range (greater than 1 micrometer diameter) to the nanoparticle range is generally unpredictable for any particular drug or class of drugs. According to the present invention, for selective cyclooxygenase-2 inhibitors of low water solubility, nanoparticulate compositions exhibit higher $C_{max}$ and/or shorter $T_{max}$ than microparticulate compositions. In one embodiment of the invention, therefore, the percentage by weight of the particles that are nanoparticles is sufficient to provide a substantially higher $C_{max}$ and/or a substantially shorter $T_{max}$ by comparison with a comparative composition wherein substantially all of the particles are larger than 1 micrometer. Preferably a composition of this embodiment has a sufficient percentage by weight of nanoparticles to provide a substantially shorter $T_{max}$, and more preferably a sufficient percentage by weight of nanoparticles to provide both a substantially higher $C_{max}$ and a substantially shorter $T_{max}$, than the comparative composition.

When administered orally to a fasting adult human, a 100 mg dose unit preferably exhibits a $T_{max}$ of less than about 90 minutes, more preferably less than about 60 minutes and preferably less than about 45 minutes, and a $C_{max}$ of at least about 100 ng/ml, more preferably at least about 200 ng/ml. Typically a composition of the invention provides a blood serum concentration of the selective cyclooxygenase-2 inhibitor of at least about 50 ng/ml within 30 minutes of oral administration; preferred compositions achieve such a concentration in as little as 15 minutes. This early rise in blood serum concentration is believed to be associated with the rapid onset of therapeutic effect achieved by compositions of the present invention.

In another embodiment of the invention, the selective cyclooxygenase-2 inhibitor, illustratively celecoxib, is present in solid particles having a $D_{90}$ particle size of about 0.01 to about 200 micrometer, wherein about 25% to 100% by weight of the particles are nanoparticles. Where the percentage by weight of nanoparticles is relatively low, for example about 25% to about 50%, preferably the $D_{90}$ particle size is about 0.01 to about 100 micrometer, more preferably about 0.01 to about 75 micrometer, still more preferably about 0.01 to about 40 micrometer, and even more preferably about 0.01 to about 25 micrometer. Particle size can vary continuously across the nanoparticulate and microparticulate range, or the composition can have a bimodal or multimodal particle size distribution, with one set of particles having a $D_{90}$ particle size less than 1 micrometer and another set of particles having a $D_{90}$ particle size substantially greater than 1 micrometer. It is generally preferred that at least about 50% by weight, and especially preferred that at least about 75% by weight, of the particles are nanoparticles. In one embodiment substantially all of the particles are smaller than 1 micrometer, i.e., the percentage by weight of nanoparticles is 100% or close to 100%.

Primary particles, generated for example by milling or grinding, or by precipitation from solution, can agglomerate to form secondary aggregate particles. The term "particle size" as used herein refers to size, in the longest dimension, of primary particles, unless the context demands otherwise.

Considering only the nanoparticulate component of a composition of the invention, average particle size is preferably about 0.1 to about 0.8 micrometer (about 100 to about 800 nm), more preferably about 0.15 to about 0.6 micrometer (about 150 to about 600 nm), and preferably about 0.2 to about 0.4 micrometer (about 200 to about 400 nm). The selective cyclooxygenase-2 inhibitor, illustratively celecoxib, can be in crystalline or amorphous form in the nanoparticles. Processes for preparing nanoparticles that involve milling or grinding typically provide the drug in crystalline form, whereas processes that involve precipitation from solution typically provide the drug in amorphous form.

Compositions of the invention comprise a selective cyclooxygenase-2 inhibitor of low water solubility, for example celecoxib, optionally together with one or more excipients selected from diluents, disintegrants, binding agents, wetting agents and lubricants. In one embodiment, nanoparticles comprising the selective cyclooxygenase-2 inhibitor have a surface-modifying agent adsorbed on the surface thereof. In another embodiment, nanoparticles of the selective cyclooxygenase-2 inhibitor are contained in a matrix formed by a polymer. Preferably at least one of the excipients is a water-soluble diluent or wetting agent. Such a water-soluble diluent or wetting agent assists in the dispersion and dissolution of the cyclooxygenase-2 inhibitor when a composition of the invention is ingested. Preferably both a water-soluble diluent and a wetting agent are present.

A composition of the invention can be a substantially homogeneous flowable mass such as a particulate or granular solid or a liquid, or it can be in the form of discrete articles such as capsules or tablets each comprising a single dose unit.

In a composition that is a substantially homogeneous flowable mass, single dose units are measurably removable using a suitable volumetric measuring device such as a spoon or cup. Suitable flowable masses include, but are not limited to, powders and granules. Alternatively, the flowable mass can be a suspension having the cyclooxygenase-2 inhibitor in a solid particulate phase dispersed in a liquid phase, preferably an aqueous phase. At least a portion of the particulate phase is nanoparticulate. In preparing such a suspension, use of a wetting agent such as polysorbate 80 or the like is likely to be beneficial. A suspension can be prepared by dispersing nanoparticulate or partially nanoparticulate cyclooxygenase-2 inhibitor in the liquid phase; alternatively the cyclooxygenase-2 inhibitor, illustratively celecoxib, can be precipitated from solution in a solvent such as an alcohol, preferably ethanol. The aqueous phase preferably comprises a palatable vehicle such as water, syrup or fruit juice, for example apple juice.

Compositions of the present invention are useful in treatment and prevention of a very wide range of disorders mediated by cyclooxygenase-2. Presently contemplated compositions are useful for, but not limited to, the treatment of inflammation in a subject, as an analgesic for example in the treatment of pain and headaches, and as an antipyretic in the treatment of fever. For example, such compositions are useful to treat arthritic disorders, including but not limited to rheumatoid arthritis, spondyloarthropathies, gouty arthritis, osteoarthritis, systemic lupus erythematosus and juvenile arthritis. Such compositions are also useful in the treatment of asthma, bronchitis, menstrual cramps, preterm labor, tendonitis, bursitis, allergic neuritis, cytomegalovirus infectivity, apoptosis including HIV-induced apoptosis, lumbago, liver disease including hepatitis, skin-related conditions such as psoriasis, eczema, acne, UV damage, burns and dermatitis, and post-operative inflammation including that following ophthalmic surgery such as cataract surgery or refractive surgery. Contemplated compositions are useful to treat gastrointestinal conditions such as inflammatory bowel disease, Crohn's disease, gastritis, irritable bowel syndrome and ulcerative colitis. Contemplated compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. Contemplated compositions are useful in the treatment of ophthalmic diseases, such as retinitis, conjunctivitis, retinopathies, uveitis, ocular photophobia, and of acute injury to the eye tissue. Contemplated compositions are useful in the treatment of pulmonary inflammation, such as that associated with viral infections and cystic fibrosis, and in bone resorption such as that associated with osteoporosis. Contemplated compositions are useful for the treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia, and senile dementia.

Compositions of the invention are especially useful as anti-inflammatory agents, such as for the treatment of arthritis, with the additional benefit of having significantly less harmful side effects than compositions of conventional nonsteroidal anti-inflammatory drugs (NSAIDs).

Contemplated compositions are useful in the treatment of allergic rhinitis, respiratory distress syndrome, endotoxin shock syndrome, and liver disease. Contemplated compositions are useful in the treatment of pain, including but not limited to postoperative pain, dental pain, muscular pain, and pain resulting from cancer.

Contemplated compositions are useful for, but not limited to, treating and preventing inflammation-related cardiovascular disorders in a subject. Such compositions are useful for treatment and prevention of vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries. Such compositions are useful for, but not limited to, the treatment of angiogenesis-related disorders in a subject. Compositions of the invention can be administered to a subject in need of angiogenesis inhibition. Such compositions are useful for the treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; and disorders of the female reproductive system such as endometriosis.

Contemplated compositions are useful for the prevention or treatment of benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreas cancer, ovary cancer, prostate cancer, cervical cancer, lung cancer, breast cancer and skin cancer, such as squamous cell and basal cell cancers. Compositions of the invention can also be used to treat the fibrosis which occurs with radiation therapy. Such compositions can be used to treat subjects having adenomatous polyps, including those with familial adenomatous polyposis (FAP). Additionally, such compositions can be used to prevent polyps from forming in patients at risk of FAP.

Compositions of the present invention possess anti-inflammatory, antipyretic and analgesic properties similar or superior to those of compositions of conventional nonsteroidal anti-inflammatory drugs. Contemplated compositions also inhibit hormone-induced uterine contractions and have potential anti-cancer effects, but with a diminished ability to induce some of the mechanism-based side effects of conventional NSAIDs. In particular, compositions of the invention have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs.

Contemplated compositions are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and injuries following surgical and dental procedures. In addition, contemplated compositions inhibit cellular neoplastic transformations and metastatic tumor growth and hence can be used in the treatment of cancer, such as cancer of the colon. Contemplated compositions are also of use in the treatment and/or prevention of cyclooxygenase mediated proliferative disorders such as may occur in diabetic retinopathy and tumor angiogenesis.

Contemplated compositions inhibit prostanoid-induced smooth muscle contraction by preventing the synthesis of contractile prostanoids and hence can be of use in the treatment of dysmenorrhea, premature labor, asthma and eosinophil-related disorders. They also can be of use in the treatment of Alzheimer's disease, for decreasing bone loss particularly in postmenopausal women (i.e., treatment of osteoporosis), and for treatment of glaucoma.

By virtue of their high cyclooxygenase-2 (COX-2) inhibitory activity and/or their specificity for inhibition of cyclooxygenase-2 over cyclooxygenase-1 (COX-1), compositions of the invention are useful as an alternative to conventional NSAIDs, particularly where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants. A brief description of the potential utility of cyclooxygenase-2 inhibitors is given in an article by John Vane, *Nature*, Vol. 367, pp. 215-216, 1994, and in an article in *Drug News and Perspectives*, Vol. 7, pp. 501-512, 1994.

Preferred uses for the pharmaceutical compositions of the present invention are for the treatment of rheumatoid arthritis and osteoarthritis, for pain management generally (particularly post-oral surgery pain, post-general surgery pain, post-orthopedic surgery pain, and acute flares of osteoarthritis), the treatment of Alzheimer's disease, and colon cancer chemoprevention.

By virtue of the rapid onset of therapeutic effect exhibited by compositions of the invention, these compositions have particular advantages over prior formulations of cyclooxygenase-2 inhibitory compounds for treatment of acute cyclooxygenase-2 mediated disorders, especially for the relief of pain.

The present compositions can be used in combination therapies with opioids and other analgesics, including narcotic analgesics, Mu receptor antagonists, Kappa receptor antagonists, non-narcotic (i.e. non-addictive) analgesics, monamine uptake inhibitors, adenosine regulating agents, cannabinoid derivatives, Substance P antagonists, neurokinin-1 receptor antagonists and sodium channel blockers, among others. Preferred combination therapies comprise use of a composition of the invention with compounds selected from morphine, meperidine, codeine, pentazocine, buprenorphine, butorphanol, dezocine, meptazinol, hydrocodone, oxycodone, methadone, DuP-747, Dynorphine A, Enadoline, RP-60180, HN-11608, E-2078, ICI-204448, acetaminophen (paracetamol), propoxyphene, nalbuphine, E-4018, filenadol, mirfentanil, amitriptyline, DuP-631, GP-531, acadesine, AKI-1, AKI-2, GP-1683, GP-3269, 4030W92, tramadol racemate and isolated (+) and (−) enantiomers, AXC-3742, SNX-111, ADL2-1294, CT-3, and CP-99994.

A dose unit containing a particular amount of a cyclooxygenase-2 inhibitor, for example celecoxib, can be selected to accommodate any desired frequency of administration used to achieve a desired daily dosage. The daily dosage and frequency of administration, and therefore the selection of appropriate dose unit, depends on a variety of factors, including the age, weight, sex and medical condition of the subject, and the nature and severity of the condition or disorder, and thus may vary widely.

In the case of celecoxib, a once-a-day or twice-a-day administration regimen to provide the required daily dosage of celecoxib exhibits improved efficacy relative to other administration regimens, for compositions of the present invention. Accordingly, once-a-day or twice-a-day oral administration of a composition of the invention is preferred for providing therapeutically or prophylactically effective inhibition of cyclooxygenase-2 mediated disorders.

For the treatment of rheumatoid arthritis, compositions of the invention can be used to provide a daily dosage of celecoxib of about 50 mg to about 1000 mg, preferably about 100 mg to about 600 mg, more preferably about 150 mg to about 500 mg, and still more preferably about 175 to about 400, for example about 200 mg. The dosage can be once a day, twice a day, three times a day, or more. For example, the dosage can be 200 mg bid. A daily dose of celecoxib of about 0.67 to about 13.3 mg/kg body weight, preferably about 1.33 to about 8.00 mg/kg body weight, more preferably about 2.00 to about 6.67 mg/kg body weight, and still more preferably about 2.33 to about 5.33 mg/kg body weight, for example about 2.67 mg/kg body weight, is generally appropriate when administered in a composition of the invention. The daily dose can be administered in one to four doses per day, preferably one or two doses per day. Administration of a composition of the invention at the rate of one 100 mg dose unit twice a day is preferred for most patients, but some patients may benefit from administration of one 200 mg dose unit or two 100 mg dose units twice a day.

For the treatment of osteoarthritis, compositions of the invention can be used to provide a daily dosage of celecoxib of about 50 mg to about 1000 mg, preferably about 100 mg to about 600 mg, more preferably about 150 mg to about 500 mg, and still more preferably about 175 to about 400, for example about 200 mg. A daily dose of celecoxib of about 0.67 to about 13.3 mg/kg body weight, preferably about 1.33 to about 8.00 mg/kg body weight, more preferably about 2.00 to about 6.67 mg/kg body weight, and still more preferably about 2.33 to about 5.33 mg/kg body weight, for example about 2.67 mg/kg body weight, is generally appropriate when administered in a composition of the invention. The daily dose can be administered in one to four doses per day, preferably one or two doses per day. Administration of a composition of the invention at the rate of one 100 mg dose unit twice a day or of one 200 mg dose unit or two 100 mg dose units once a day is preferred.

For the treatment of Alzheimer's disease, compositions of the invention can be used to provide a daily dosage of celecoxib of about 50 mg to about 1000 mg, preferably about 100 mg to about 800 mg, more preferably about 150 mg to about 600 mg, and still more preferably about 175 to about 400, for example about 400 mg. A daily dose of about 0.67 to about 13.3 mg/kg body weight, preferably about 1.33 to about 10.67 mg/kg body weight, more preferably about 2.00 to about 8.00 mg/kg body weight, and still more preferably about 2.33 to about 5.33 mg/kg body weight, for example about 5.33 mg/kg body weight, is generally appropriate when administered in a composition of the invention. The daily dose can be administered in one to four doses per day, preferably one or two doses per day. Administration of a composition of the invention at the rate of one 200 mg dose unit or two 100 mg dose units twice a day is preferred for most patients.

For the treatment of cancer, compositions of the invention can be used to provide a daily dosage of celecoxib of about 50 mg to about 1000 mg, preferably about 100 mg to about 800 mg, more preferably about 150 mg to about 600 mg, and still more preferably about 175 to about 400, for example about 400 mg. A daily dose of about 0.67 to about 13.3 mg/kg body weight, preferably about 1.33 to about 10.67 mg/kg body weight, more preferably about 2.00 to about 8.00 mg/kg body weight, and still more preferably about 2.33 to about 5.33 mg/kg body weight, for example about 5.33 mg/kg body weight, is generally appropriate when administered in a composition of the invention. The daily dose can be administered in one to four doses per day, preferably two doses per day. Administration of a composition of the invention at the rate of one 200 mg dose unit or two 100 mg dose units twice a day is preferred for most patients.

For pain management, compositions of the invention can be used to provide a daily dosage of celecoxib of about 50 mg to about 1000 mg, preferably about 100 mg to about 600 mg, more preferably about 150 mg to about 500 mg, and still more preferably about 175 to about 400, for example about 200 mg. A daily dose of celecoxib of about 0.67 to about 13.3 mg/kg body weight, preferably about 1.33 to about 8.00 mg/kg body weight, more preferably about 2.00 to about 6.67 mg/kg body weight, and still more preferably about 2.33 to about 5.33 mg/kg body weight, for example about 2.67 mg/kg body weight, is generally appropriate when administered in a composition of the invention. The daily dose can be administered in one to four doses per day. Administration of a composition of the invention at the rate of one 50 mg dose unit four times a day, one 100 mg dose unit or two 50 mg dose units twice a day or one 200 mg dose unit, two 100 mg dose units or four 50 mg dose units once a day is preferred.

In general, a composition of the invention is preferably administered at a dose and frequency suitable to provide an average blood serum concentration of celecoxib of at least about 100 ng/ml in a subject over a period of about 24 hours after administration.

While the amount of celecoxib in compositions of the invention preferably is in a range disclosed herein, the compositions also may be useful for the administration of an amount of celecoxib falling outside the disclosed dosage ranges. For other selective cyclooxygenase-2 inhibitors, appropriate doses can be selected by reference to the patent literature cited hereinabove.

Nanoparticles comprising or consisting essentially of a selective cyclooxygenase-2 inhibitory compound of low water solubility, such as celecoxib, deracoxib, valdecoxib or rofecoxib, can be prepared according to any process previously applied to the preparation of other poorly water-soluble drugs in nanoparticulate form. Suitable processes, without restriction, are illustratively disclosed for such other drugs in above cited U.S. Pat. Nos. 4,826,689, 5,145,684, 5,298,262, 5,302,401, 5,336,507, 5,340,564, 5,346,702, 5,352,459, 5,354,560, 5,384,124, 5,429,824, 5,510,118, 5,518,738, 5,503,723, 5,534,270, 5,536,508, 5,552,160, 5,560,931, 5,560,932, 5,565,188, 5,569,448, 5,571,536, 5,573,783, 5,580,579, 5,585,108, 5,587,143, 5,591,456, 5,662,883, 5,665,331, 5,718,919 and 5,747,001, and above-cited International Publication Nos. WO 93/25190, WO 96/24336 and WO 98/35666, the pertinent disclosure of all of which is hereby incorporated by reference. One of ordinary skill in the art will readily adapt the processes therein described to the preparation of a poorly water-soluble selective cyclooxygenase-2 inhibitor, for example celecoxib, deracoxib, valdecoxib or rofecoxib, in nanoparticulate form.

Any excipients employed in a composition of the invention can be solids or liquids or both. The composition preferably contains about 1% to about 95%, preferably about 10% to about 90%, more preferably about 25% to about 85%, and still more preferably about 30% to about 80%, by weight of the selective cyclooxygenase-2 inhibitor, illustratively celecoxib. Compositions of the invention containing excipients can be prepared by any of the well known techniques of pharmacy that comprise admixing the excipients with a drug or therapeutic agent, except that in the present case the drug or therapeutic agent, namely a selective cyclooxygenase-2 inhibitor, is at least partially pre-prepared, optionally together with one or more excipients, in nanoparticulate form as indicated above.

A composition of the invention contains a desired amount of a cyclooxygenase-2 inhibitor, illustratively celecoxib, per dose unit and can be in the form of, for example, a tablet, a pill, a hard or soft capsule, a lozenge, a cachet, a dispensable powder, granules, a suspension, an elixir, a liquid, or any other form reasonably adapted for oral administration. Such a composition is preferably made in the form of discrete dose units each containing a predetermined amount of the cyclooxygenase-2 inhibitor, such as tablets or capsules. These oral dosage forms may further comprise, for example, buffering agents. Tablets, pills and the like additionally can be prepared with or without coatings.

Compositions of the invention suitable for buccal or sublingual administration include, for example, lozenges comprising the cyclooxygenase-2 inhibitor in a flavored base, such as sucrose, and acacia or tragacanth, and pastilles comprising the cyclooxygenase-2 inhibitor in an inert base such as gelatin and glycerin or sucrose and acacia.

Liquid dosage forms for oral administration include pharmaceutically acceptable suspensions, syrups, and elixirs containing inert diluents commonly used in the art, such as water. Such compositions may also comprise, for example, wetting agents, emulsifying and suspending agents, and sweetening, flavoring, and perfuming agents.

As indicated above, excipient-containing compositions of the invention can be prepared by any suitable method of pharmacy, which includes the step of bringing into association the cyclooxygenase-2 inhibitor, at least partially in nanoparticulate form, and the excipient(s). In general, such compositions are prepared by uniformly and intimately admixing the partially or wholly nanoparticulate cyclooxygenase-2 inhibitory compound (hereinafter sometimes referred to as the "nanoparticulate compound") with a liquid or finely divided diluent, or both, and then, if necessary or desired, encapsulating or shaping the product. For example, a tablet can be prepared by compressing or molding a powder or granules of the nanoparticulate compound, together with one or more excipients. Compressed tablets can be prepared by compressing, in a suitable machine, a free-flowing composition, such as a powder or granules, comprising the nanoparticulate compound optionally mixed with one or more binding agent(s), lubricant(s), inert diluent(s), wetting agent(s) and/or dispersing agent(s). Molded tablets can be made by molding, in a suitable machine, the nanoparticulate compound moistened with an inert liquid diluent.

As noted above, compositions of the present invention comprise a partially or wholly nanoparticulate selective cyclooxygenase-2 inhibitory compound, illustratively celecoxib, in a therapeutically or prophylactically effective amount per dose unit in combination with one or more pharmaceutically acceptable excipients appropriate for oral administration. Compositions of the present invention preferably comprise the nanoparticulate compound in a desired amount admixed with one or more excipients selected from the group consisting of pharmaceutically acceptable diluents, disintegrants, binding agents, adhesives, wetting agents, lubricants, and anti-adherent agents. In addition, the nanoparticles themselves can optionally contain one or more matrix polymers and/or surface modifying agents as disclosed in several of the above-cited references. More preferably, such compositions are tableted or encapsulated for convenient administration in the form of immediate release capsules or tablets.

Through appropriate selection and combination of excipients, compositions can be provided exhibiting improved performance with respect to, among other properties, efficacy, bioavailability, clearance time, stability, compatibility of celecoxib and carrier materials, safety, dissolution profile, disintegration profile and/or other pharmacokinetic, chemical and/or physical properties. The excipients preferably are water-soluble or water dispersible and have wetting properties to offset the low aqueous solubility and hydrophobicity of the cyclooxygenase-2 inhibitor. Where the composition is formulated as a tablet, the combination of excipients selected provides tablets that can exhibit improvement, among other properties, in dissolution and disintegration profiles, hardness, crushing strength, and/or friability.

Compositions of the invention optionally comprise one or more pharmaceutically acceptable diluents as excipients. Suitable diluents include, either individually or in combination, lactose USP; lactose USP, anhydrous; lactose USP, spray dried; starch USP; directly compressible starch; mannitol USP; sorbitol; dextrose monohydrate; microcrystalline cellulose NF; dibasic calcium phosphate dihydrate NF; sucrose-based diluents; confectioner's sugar; monobasic calcium sulfate monohydrate; calcium sulfate dihydrate NF; calcium lactate trihydrate granular NF; dextrates, NF (e.g., Emdex); Celutab; dextrose (e.g., Cerelose); inositol; hydrolyzed cereal solids such as the Maltrons and Mor-Rex; amylose; Rexcel; powdered cellulose (e.g., Elcema); calcium carbonate; glycine; bentonite; polyvinylpyrrolidone; and the like. Such diluents, if present, constitute in total about 5% to about 99%, preferably about 10% to about 85%, and more preferably about 20% to about 80%, of the total weight of the composition. The diluent or diluents selected preferably exhibit suitable flow properties and, where tablets are desired, compressibility.

Lactose and microcrystalline cellulose, either individually or in combination, are preferred diluents. Both diluents are chemically compatible with celecoxib. The use of extragranular microcrystalline cellulose (that is, microcrystalline cellulose added to a wet granulated composition after the drying step) can be used to improve hardness (for tablets) and/or disintegration time. Lactose, especially lactose monohydrate, is particularly preferred. Lactose typically provides compositions having suitable release rates of the cyclooxygenase-2 inhibitor, stability, pre-compression flowability, and/or drying properties at a relatively low diluent cost. It provides a high density substrate that aids densification during granulation (where wet granulation is employed) and therefore improves blend flow properties.

Compositions of the invention optionally comprise one or more pharmaceutically acceptable disintegrants as excipients, particularly for tablet formulations. Suitable disintegrants include, either individually or in combination, starches; sodium starch glycolate; clays (such as Veegum HV); celluloses (such as purified cellulose, methylcellulose, sodium carboxymethylcellulose and carboxymethylcellulose); alginates; pregelatinized corn starches (such as National 1551 and National 1550); crospovidone USP NF; and gums (such as agar, guar, locust bean, Karaya, pectin, and tragacanth). Disintegrants may be added at any suitable step during the preparation of the composition, particularly prior to granulation or during the lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 6%, and still more preferably about 0.2% to about 5%, of the total weight of the composition. Croscarmellose sodium confers superior intragranular disintegration capabilities to compositions of the present invention.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starch; cellulose materials such as, but not limited to, methylcellulose and sodium carboxymethylcellulose (e.g., Tylose); alginic acid and salts of alginic acid; magnesium aluminum silicate; polyethylene glycol; guar gum; polysaccharide acids; bentonites; polyvinylpyrrolidone; polymethacrylates; hydroxypropylmethylcellulose (HPMC); hydroxypropylcellulose (Klucel); ethylcellulose (Ethocel); pregelatinized starch (such as National 1511 and Starch 1500). Such binding agents and/or adhesives, if present, constitute in total about 0.5% to about 25%, preferably about 0.75% to about 15%, and more preferably about 1% to about 10%, of the total weight of the composition.

Polyvinylpyrrolidone is a preferred binding agent used to impart cohesive properties to a powder blend of the cyclooxygenase-2 inhibitor and other excipients for granulation. Polyvinylpyrrolidone, if present, preferably constitutes about 0.5% to about 10%, more preferably about 0.5% to about 7%, and still more preferably about 0.5% to about 5% of the total weight of the composition. Polyvinylpyrrolidone viscosities up to about 20 cPs may be used although viscosities of about 6 cPs or lower are preferred, particularly about 3 cPs or lower. Polyvinylpyrrolidone provides cohesiveness to the powder blend and facilitates the necessary binding to form granules during wet granulation.

The cyclooxygenase-2 inhibitory compounds used in the present invention, in particular celecoxib, are largely insoluble in aqueous solution. Accordingly, compositions of the invention optionally but preferably comprise one or more pharmaceutically acceptable wetting agents as excipients. Such wetting agents are preferably selected to maintain the cyclooxygenase-2 inhibitor in close association with water, a condition that is believed to improve the relative bioavailability of the composition. Suitable wetting agents include, either individually or in combination, oleic acid; glyceryl monostearate; sorbitan monooleate; sorbitan monolaurate; triethanolamine oleate; polyoxyethylene sorbitan monooleate; polyoxyethylene sorbitan monolaurate; sodium oleate; and sodium lauryl sulfate. Wetting agents that are anionic surfactants are preferred. Such wetting agents, if present, constitute in total about 0.25% to about 15%, preferably about 0.4% to about 10%, and more preferably about 0.5% to about 5%, of the total weight of the composition.

Sodium lauryl sulfate is a preferred wetting agent. Sodium lauryl sulfate, if present, constitutes about 0.25% to about 7%, more preferably about 0.4% to about 6%, and still more preferably about 0.5 to about 5% of the total weight of the composition.

Compositions of the invention optionally comprise one or more pharmaceutically acceptable lubricants and/or glidants as excipients. Suitable lubricants and/or glidants include, either individually or in combination, glyceryl behapate (Compritol 888); stearates (magnesium, calcium, and sodium); stearic acid; hydrogenated vegetable oils (e.g., Sterotex); talc; waxes; Stearowet; boric acid; sodium benzoate; sodium acetate; sodium fumarate; sodium chloride; DL-leucine; polyethylene glycols (e.g., Carbowax 4000 and Carbowax 6000); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the composition.

Magnesium stearate is a preferred lubricant used, for example, to reduce friction between the equipment and granulated mixture during compression of tablet formulations.

Other excipients (such as anti-adherent agents, colorants, flavors, sweeteners and preservatives) are known in the pharmaceutical art and can be included in compositions of the invention. For example, iron oxide can be added to the composition to provide a yellow color.

In one embodiment of the present invention, the composition is in the form of unit dose capsules or tablets and comprises a partially or wholly nanoparticulate selective cyclooxygenase-2 inhibitor, illustratively celecoxib, in a desired amount together with a binding agent. Such a composition preferably further comprises one or more excipients selected from the group consisting of pharmaceutically acceptable diluents, disintegrants, binding agents, wetting agents and lubricants. More preferably, the composition comprises one or more excipients selected from the group consisting of lactose, sodium lauryl sulfate, polyvinylpyrrolidone, croscarmellose sodium, magnesium stearate and microcrystalline cellulose. Still more preferably, the composition comprises lactose monohydrate and croscarmellose sodium. Even more preferably, the composition further comprises one or more of the carrier materials sodium lauryl sulfate, magnesium stearate and microcrystalline cellulose.

Although unit dose capsule and tablet compositions of the invention can be prepared, for example, by direct encapsulation or direct compression, they preferably are wet granulated prior to encapsulation or compression. Wet granulation, among other effects, densifies milled compositions resulting in improved flow properties, improved compression characteristics and easier metering or weight dispensing of the compositions for encapsulation or tableting. The secondary particle size resulting from granulation (i.e., granule size) is not narrowly critical, it being important only that the average granule size preferably is such as to allow for convenient handling and processing and, for tablets, to permit the formation of a directly compressible mixture that forms pharmaceutically acceptable tablets.

The desired tap and bulk densities of the granules are normally about 0.3 g/ml to about 1.0 g/ml.

Excipients for capsule and tablet compositions of the invention preferably are selected to provide a disintegration time of less than about 30 minutes, preferably about 25 minutes or less, more preferably about 20 minutes or less, and still more preferably about 15 minutes or less.

For tablet formulations, the complete mixture in an amount sufficient to make a uniform batch of tablets is subjected to tableting in a conventional production scale tableting machine at normal compression pressure (for example, applying a force of about 1 kN to about 50 kN in a typical tableting die). Any tablet hardness convenient with respect to handling, manufacture, storage and ingestion may be employed. For 100 mg tablets, hardness is preferably at least 4 kP, more preferably at least about 5 kP, and still more preferably at least about 6 kP. For 200 mg tablets, hardness is preferably at least 7 kP, more preferably at least about 9 kP, and still more preferably at least about 11 kP. The mixture, however, is not to be compressed to such a degree that there is subsequent difficulty in achieving hydration when exposed to gastric fluid.

For tablet formulations, tablet friability preferably is less than about 1.0%, more preferably less than 0.8%, and still more preferably less than about 0.5% in a standard test.

The present invention also is directed to a therapeutic method of treating a condition or disorder where treatment with a cyclooxygenase-2 inhibitor is indicated, the method comprising oral administration of one or more dose units of a composition of the invention to a subject in need thereof. The dosage regimen to prevent, give relief from, or ameliorate the condition or disorder preferably corresponds to the once-a-day or twice-a-day treatments discussed above, but can be modified in accordance with a variety of factors. These include the type, age, weight, sex, diet, and medical condition of the subject and the nature and severity of the disorder. Thus, the dosage regimen actually employed can vary widely and can therefore deviate from the preferred dosage regimens set forth above.

Initial treatment of a subject suffering from a condition or disorder where treatment with a cyclooxygenase-2 inhibitor is indicated can begin with the dosages indicated above. Treatment is generally continued as necessary over a period of several weeks to several months or years until the condition or disorder has been controlled or eliminated. Subjects undergoing treatment with a composition of the invention can be routinely monitored by any of the methods well known in the art to determine the effectiveness of therapy. Continuous analysis of such data permits modification of the treatment regimen during therapy so that optimally effective amounts of the cyclooxygenase-2 inhibitor are administered at any point in time, and so that the duration of treatment can be determined as well. In this way, the treatment regimen/dosing schedule can be rationally modified over the course of therapy so that the lowest amount of the cyclooxygenase-2 inhibitor exhibiting satisfactory effectiveness is administered, and so that administration is continued only so long as is necessary to successfully treat the condition or disorder.

The present invention also is directed to methods for the preparation of compositions comprising a poorly water soluble selective cyclooxygenase-2 inhibitor, illustratively celecoxib, partially or wholly in nanoparticulate form in accordance with the invention. More particularly, the invention is directed to methods for preparing such compositions in the form of discrete unit dose tablets or capsules, such that each tablet or capsule contains an amount of the cyclooxygenase-2 inhibitor sufficient to provide rapid onset of therapeutic effect as described hereinabove, and preferably a continuing therapeutic effect for about 12 to 24 hours. Each tablet or capsule preferably contains about 50 mg to about 200 mg, for example about 50 mg, about 100 mg or about 200 mg, of the cyclooxygenase-2 inhibitor, illustratively celecoxib. According to the present invention, wet granulation, dry granulation or direct compression or encapsulation methods can be employed to prepare tablet or capsule compositions of the invention.

Wet granulation is a preferred method of preparing pharmaceutical compositions of the present invention. In the wet granulation process, any portion of the cyclooxygenase-2 inhibitor that is not to be included in nanoparticulate form (if desired, together with one or more carrier materials) is initially milled or micronized to a desired range of particle sizes greater than 1 micrometer. Although various conventional mills or grinders can be used, impact milling such as pin milling of the drug provides improved blend uniformity to the final composition relative to other types of milling. Cooling of the material being milled, for example, using liquid nitrogen, may be necessary during milling to avoid heating the cyclooxygenase-2 inhibitor to undesirable temperatures. The $D_{90}$ particle size during this milling step is preferably reduced to less than about 25 micrometer.

The milled or micronized cyclooxygenase-2 inhibitor, if any, is then blended with the desired amount of the cyclooxygenase-2 inhibitor in nanoparticulate form, prepared by any process known in the art as indicated hereinabove to provide a partially or wholly nanoparticulate cyclooxygenase-2 inhibitory compound ("the nanoparticulate compound"). Simultaneously or thereafter, the nanoparticulate compound is blended, for example in a high shear mixer/granulator, planetary mixer, twin-shell blender or sigma mixer, with one or more excipients, including excipients that have been milled together with the celecoxib or are present in the nanoparticles, to form a dry powder mixture. Typically, the nanoparticulate compound is blended with one or more diluent(s), disintegrant(s) and/or binding agent(s) and, optionally, one or more wetting agent(s) in this step, but alternatively all or a portion of one or more of the excipients can be added in a later step. For example, in tablet formulations where croscarmellose sodium is employed as a disintegrant, it has been discovered that addition of a portion of the croscarmellose sodium during the blending step (providing intragranular croscarmellose sodium) and addition of the remaining portion after the drying step discussed below (providing extragranular croscarmellose sodium) can improve disintegration of the tablets produced. In this situation, preferably about 60% to about 75% of the croscarmellose sodium is added intragranularly and about 25% to about 40% of the croscarmellose sodium is added extragranularly. Similarly, for tablet formulations it has been discovered that addition of microcrystalline cellulose after the drying step below (extragranular microcrystalline cellulose) can improve compressibility of the granules and hardness of the tablets prepared from the granules.

This blending step of the process preferably comprises blending of nanoparticulate compound, lactose, polyvinylpyrrolidone and croscarmellose sodium. It has been discovered that blending times as short as three minutes can provide a dry powder mixture having a sufficiently uniform distribution of the cyclooxygenase-2 inhibitor.

Water, preferably purified water, is then added to the dry powder mixture and the mixture is blended for an additional period of time, to form a wet granulated mixture. Preferably a wetting agent is used, and this is preferably first added to the water and mixed for at least 15 minutes, preferably at least 20 minutes, prior to adding the water to the dry powder mixture. The water can be added to the mixture at once, gradually over a period of time, or in several portions over a period of time. The water preferably is added gradually over a period of time. Alternatively, the wetting agent can be added to the dry powder mixture and water then can be added to the resulting mixture. An additional period of mixing after the water addition is complete is preferred to ensure the uniform distribution of the water in the mixture.

The wet granulated mixture preferably is then wet milled, for example with a screening mill, to eliminate large agglomerations of material that form as a by-product of the wet granulation operation. If not removed, these agglomerations would prolong the subsequent fluidized bed drying operation and increase the variation with respect to moisture control.

The wet granulated or wet milled mixture is then dried, for example, in an oven or a fluidized bed dryer, preferably a fluidized bed drier, to form dry granules. If desired, the wet granulated mixture can be extruded or spheronized prior to drying. For the drying process, conditions such as inlet air temperature and drying time are adjusted to achieve the desired moisture content for the dry granules. It may be desirable to combine two or more granulation sections for this drying step and subsequent processing steps.

To the extent necessary, the dry granules are then reduced in size in preparation for compression or encapsulation. Conventional particle size reduction equipment such as oscillators or impact mills (such as Fitz mills) can be employed.

A slight decrease in granule size has been observed as mixing time increases for mixtures containing lower water amounts. It is hypothesized that where the water concentration is too low to fully activate the binding agent employed, the cohesive forces between the primary particles within the granules are insufficient to survive the shearing forces generated by the mixing blades and granule size attrition rather than growth occurs. Conversely, increasing the amount of water to fully activate the binding agent allows cohesive forces between the primary particles to survive the shearing forces generated by the mixing blades and granule growth rather than attrition occurs with increased mixing time and/or water addition rate. Variation of the screen size of the wet mill tends to have a greater impact on the granule size than variation of the feed rate and/or mill speed.

The dry granules are then placed in a suitable blender, such as a twin-shell blender, and optionally a lubricant (such as magnesium stearate) and any additional carrier materials are added (such as extragranular microcrystalline cellulose and/or extragranular croscarmellose sodium in certain tablet formulations) to form a final blended mixture. Where the diluents include microcrystalline cellulose, the addition of a portion of the microcrystalline cellulose during this step has been found to materially increase granule compressibility and tablet hardness. However, increasing the amount of magnesium stearate above about 1% to about 2% tends to decrease tablet hardness and increase friability and dissolution time.

This final blended mixture is then encapsulated (or, if tablets are to be prepared, compressed into tablets of the desired weight and hardness using appropriately sized tooling). Conventional compression and encapsulation techniques known to those of ordinary skill in the art can be employed. Suitable results are obtained for capsules by employing bed heights ranging from about 20 mm to about 60 mm, compaction settings ranging from about 0 to about 5 mm, and speeds from about 60,000 capsules per hour to about 130,000 capsules per hour. Slug formation can be minimized or eliminated by using the lowest compaction setting at which capsule weight control can be maintained. Where coated tablets are desired, conventional coating techniques known to those of ordinary skill in the art can be employed.

This combination of unit operations produces granules that are uniform in cyclooxygenase-2 inhibitor, illustratively celecoxib, content at the unit dose level, that readily disintegrate, that flow with sufficient ease so that weight variation can be reliably controlled during capsule filling or tableting, and that are dense enough in bulk so that the batch can be processed in the selected equipment and individual doses fit into the specified capsules or tablet dies.

The present invention also is directed to use of compositions of the invention in preparation of medicaments useful in the treatment and/or prophylaxis of cyclooxygenase-2 mediated conditions and disorders, in particular such conditions and disorders where rapid onset of therapeutic effect is desired or required.

The present invention also embodies a novel solid state form of celecoxib, Form I celecoxib. The present invention further embodies another solid state form of celecoxib, Form II celecoxib. Each of these novel solid state forms includes solvated crystalline forms, non-solvated and non-hydrated crystalline forms. These novel forms of celecoxib described in the present application possess one or more of the above-described advantageous chemical and/or physical properties relative to the other solid state forms described herein or otherwise disclosed in the literature.

In one embodiment of the invention, the solid state form comprises Form I celecoxib. Without limiting the invention, it is believed that Form I celecoxib has higher solubility and a more rapid rate of dissolution than Form III, because Form III is more thermodynamically stable than Form I and because Form III has a lower free energy than Form I. A rapid rate of dissolution is useful because increasing the rate of dissolution of a drug typically increases its bioavailability.

Form I celecoxib is a crystalline form of celecoxib having an X-ray powder diffraction pattern with peaks at about 5.5, 5.7, 7.2, and 16.6 degrees two theta. Form I celecoxib has an X-ray powder diffraction pattern substantially as shown in the top trace in FIG. 1a. Form I celecoxib has a melting point of about 162.5° C. to about 163° C., preferably about 162.8° C. Form I celecoxib has a differential scanning calorimetry endotherm maximum at about 163.3° C. when scanned at 0.5° C./min as FIG. 3. Form I celecoxib is characterized by the IR spectrum shown in FIG. 2, with a peak between about 3250 and 3260 $cm^{-1}$, and another between 3350 and 3360 $cm^{-1}$, preferably the peaks are at about 3256 $cm^{-1}$ and 3356 $cm^{-1}$, respectively. The solid form of the present invention has a phase purity of at least about 5% Form I celecoxib, preferably at least about 10% Form I celecoxib, more preferably at least about 25% Form I celecoxib, still more preferably at least about 50% Form I celecoxib, yet more preferably at least about 75% Form I celecoxib, more preferably still at least about 90%, and still more preferably having a substantially phase pure form of Form I celecoxib.

In another embodiment of the invention, a pharmaceutical composition is provided which comprises a therapeutically-effective amount of a solid form of celecoxib and at least one pharmaceutically-acceptable carrier, adjuvant or diluent, wherein the solid form of celecoxib comprises at least 2% Form I celecoxib, and preferably 10% Form I celecoxib, or more preferably 50% Form I celecoxib, and still more preferably 98% Form I celecoxib. In one preferred embodiment, the solid form of celecoxib is predominantly Form I celecoxib.

In yet another embodiment of the present invention, a method is described of treating or preventing a cyclooxygenase-2-mediated condition or disorder in a subject, the method comprising administering to a subject a therapeutically-effective amount of Form I celecoxib. Preferably the cyclooxygenase-2-mediated condition or disorder to be treated or prevented is pain, inflammation, arthritis, tumor growth, metastasis, or familial adenomatous polyposis.

Still another embodiment of the invention is a method of preparing Form I celecoxib wherein the method comprises crystallizing Form I celecoxib from a mixture of celecoxib and a solvent, wherein the crystallization is performed at a temperature above the enantiotropic transition temperature of Form I celecoxib. Prior to the crystallization of Form I celecoxib, the solvent may be seeded with a seed crystal of Form I celecoxib, resulting in the production of Form I celecoxib with at least about 5 weight percent phase purity, preferably at least about 10 weight percent phase purity, more preferably at least about 25 weight percent phase purity, more preferably at least about 50 weight percent phase purity, and still more preferably at least about 90 weight percent phase purity.

The present invention is also directed to the preparation of a crystalline form of celecoxib wherein the method comprises heating a solvate of celecoxib thereby producing Form I celecoxib. The solvate can be heated for example, to a temperature of about 50° C. to about 160° C., preferably to a temperature of about 60° C. to about 150° C., more preferably to a temperature of about 70° C. to about 140° C., still more preferably to a temperature of about 80° C. to about 130° C., yet more preferably to a temperature of about 85° C. to about 120° C., more preferably still to a temperature of about 90° C. to about 110° C., and more preferably to a temperature of about 100° C. The heating can be performed over any convenient period of time, for example for more than about 1 minute, preferably for more than about 5 minutes, more preferably for more than about 60 minutes, still more preferably for about 2 hours and more preferably still for about 4 hours or longer. Furthermore, this method may be performed at any pressure, preferably below atmospheric pressure. The solvate used in the present invention comprises celecoxib and a solvent. For example, the solvent can be an amide solvent. Useful amide solvents include N,N-dimethylformamide, N,N-dimethylacetamide, 1-methyl-2-pyrrolidinone, 1,3-dimethyl-3,4,5,6-tetrahydro-2(1H)-pyrimidinone, and 1,1,3,3-tetramethylurea, or any mixture of these solvents. A preferred solvent is 1,1,3,3-tetramethylurea. Another preferred solvent is 1,3-dimethyl-3,4,5,6-tetrahydro-2(1H)-pyrimidinone. Still another preferred solvent is 1-methyl-2-pyrrolidinone. Still another preferred solvent is N,N-dimethylformamide. Still another preferred solvent is N,N-dimethylacetamide.

The solvate can be prepared by a process comprising mixing celecoxib with an amide solvent selected from the group consisting of N,N-dimethylformamide, N,N-dimethylacetamide, 1-methyl-2-pyrrolidinone, 1,3-dimethyl-3,4,5,6-tetrahydro-2(1H)-pyrimidinone, and 1,1,3,3-tetramethylurea, or any mixture of these solvents. A preferred solvent is 1,1,3,3-tetramethylurea. Another preferred solvent is 1,3-dimethyl-3,4,5,6-tetrahydro-2(1H)-pyrimidinone. Still another preferred solvent is 1-methyl-2-pyrrolidinone. Still another preferred solvent is N,N-dimethylformamide. Still another preferred solvent is N,N-dimethylacetamide.

The present invention is also directed to a method of producing Form I celecoxib wherein the method comprises milling or grinding Form III celecoxib. A useful milling step can include for example, wet milling or ball milling. A useful grinding step can include for example, grinding or shaking.

The present invention is also directed to a method of producing Form I celecoxib wherein the method comprises milling or grinding a celecoxib solvate. A useful milling step can include for example, wet milling or ball milling. A useful grinding step can include for example, grinding or shaking.

Another embodiment of the present invention is a method of producing Form I celecoxib wherein the method comprises melting Form II celecoxib and cooling the melt thereby producing Form I celecoxib.

Another embodiment of the present invention is a method of producing Form I celecoxib wherein the method comprises melting Form III celecoxib and cooling the melt thereby producing Form I celecoxib.

The present invention is also directed to a method of producing Form I celecoxib wherein the method comprises evaporating solvent from a celecoxib solution. For example the solvent can be an ether or a hydrocarbon, or a mixture of an ether and a hydrocarbon. Preferably the solvent comprises ethyl acetate and heptane, preferably at a ratio of 15:85. The present method can be performed at any pressure, preferably below atmospheric pressure. The method can be performed over a wide range of temperatures, preferably at about 35° C.

In another embodiment of the invention, the solid state form comprises Form II celecoxib. Without limiting the invention, it is believed that Form II celecoxib has higher solubility and a more rapid rate of dissolution than Form III, because Form III is more thermodynamically stable than Form II and because Form III has a lower free energy than Form II. A rapid rate of dissolution is useful because increasing the rate of dissolution of a drug typically increases its bioavailability.

Form II celecoxib has an X-ray powder diffraction pattern with a peaks at about 10.3, 13.8, 17.7 degrees two theta. A mixture of Form I and Form II has the peaks as shown in the top trace in FIG. 1b. Form II celecoxib has a melting point of about 161° C. to about 162° C., preferably about 161.5° C. Form II celecoxib has a differential scanning calorimetry endotherm maximum at about 162.0° C. when scanned at 0.5° C./min. Form II celecoxib is expected to have higher solubility and more rapid dissolution than Form III celecoxib. The solid form of the present invention has a phase purity of at least about 5% Form II celecoxib, preferably at least about 10% Form II celecoxib, more preferably at least about 25% Form II celecoxib, still more preferably at least about 50% Form II celecoxib, yet more preferably at least about 75% Form II celecoxib, yet still more preferably at least about 90%, and still more preferably having a substantially phase pure form of Form II celecoxib.

In another embodiment of the invention, a pharmaceutical composition is provided which comprises a therapeutically-effective amount of a solid form of celecoxib and at least one pharmaceutically-acceptable carrier, adjuvant or diluent, wherein the solid form of celecoxib comprises at least 2% Form II celecoxib, and preferably 10% Form II celecoxib, or more preferably 50% Form II celecoxib, still more preferably 98% Form II celecoxib. In one preferred embodiment, the solid form of celecoxib is predominantly Form II celecoxib.

In yet another embodiment of the present invention, a method is described of treating or preventing a cyclooxygenase-2-mediated condition or disorder in a subject, the method comprising administering to a subject a therapeutically-effective amount of Form II celecoxib. Preferably the cyclooxygenase-2-mediated condition or disorder to be treated or prevented is pain, inflammation, arthritis, tumor growth, metastasis, or familial adenomatous polyposis.

Still another embodiment of the invention is a method of preparing Form II celecoxib from a mixture comprising celecoxib and a solvent wherein the crystallization is performed at a temperature above the enantiotropic transition temperature of Form II celecoxib thereby producing Form II celecoxib. Prior to the crystallization of Form II celecoxib, the solvent may be seeded with a seed crystal of Form II celecoxib, resulting in the production of Form II celecoxib with at least about 5% weight percent phase purity, preferably at least about 10% weight percent phase purity, and more preferably at least about 25% weight percent phase purity.

The present invention is also directed to the preparation of a crystalline form of celecoxib wherein the method involves heating a solvate of celecoxib thereby producing Form II celecoxib. The solvate can be heated for example, to a temperature of about 50° C. to about 160° C., preferably to a temperature of about 60° C. to about 145° C., more preferably to a temperature of about 70° C. to about 140° C., still more preferably to a temperature of about 80° C. to about 140° C., yet more preferably to a temperature of about 90° C. to about 140° C., yet more preferably to a temperature of about 100° C. to about 140° C., more preferably to a temperature of about 110° C. to about 140° C., more preferably still to a temperature of about 120° C. to about 140° C., more preferably to a temperature of about 125° C. to about 135° C., and more preferably still to a temperature of about 130° C. The heating can be performed over any convenient period of time, for example for more than about 1 minute, preferably for more than about 5 minutes, preferably for more than about 60 minutes, still more preferably for about 2 hours and preferably for about 4 hours or longer. Furthermore, this method may be performed at any pressure, preferably below atmospheric pressure. The solvate used in the present invention comprises celecoxib and a solvent. For example, the solvent can be an amide solvent. Useful amide solvents include N,N-dimethylformamide, N,N-dimethylacetamide, 1-methyl-2-pyrrolidinone, 1,3dimethyl-3,4,5,6-tetrahydro-2(1H)-pyrimidinone, and 1,1,3,3-tetramethylurea, or any mixture of these solvents. A preferred solvent is 1,1,3,3-tetramethylurea. Another preferred solvent is 1,3-dimethyl-3,4,5,6-tetrahydro-2(1H)-pyrimidinone. Still another preferred solvent is 1-methyl-2-pyrrolidinone. Still another preferred solvent is N,N-dimethylformamide. Still another preferred solvent is N,N-dimethylacetamide.

In another embodiment of the present invention, wherein Form II celecoxib is prepared by heating a solvate of celecoxib to produce Form II celecoxib, the solvate is prepared by a process comprising mixing celecoxib with an amide solvent selected from a group consisting of N,N-dimethylformamide, N,N-dimethylacetamide, 1-methyl-2-pyrrolidinone, 1,3-dimethyl-3,4,5,6-tetrahydro-2(1H)-pyrimidinone, and 1,1,3, 3-tetramethylurea, or any mixture of these solvents, preferably 1,1,3,3-tetramethylurea, more preferably 1,3-dimethyl-3,4,5,6-tetrahydro-2(1H)-pyrimidinone, still more preferably 1-methyl-2-pyrrolidinone, yet more preferably N,N-dimethylformamide, and preferably, N,N-dimethylacetamide.

Another embodiment of the present invention is a solid form of celecoxib comprised of Form I celecoxib and Form II celecoxib.

Still another embodiment of the present invention is a solid form of celecoxib comprising Form I celecoxib and Form III celecoxib.

Yet another embodiment of the present invention is a solid form of celecoxib comprising Form II celecoxib and Form III celecoxib.

Still yet another embodiment of the present invention is a solid form of celecoxib comprising Form I celecoxib, Form II celecoxib and Form III celecoxib.

The present invention is also directed to a method of producing Form II celecoxib wherein the method comprises milling or grinding Form III celecoxib. A useful milling step can include for example, wet milling or ball milling. A useful grinding step can include for example, grinding or shaking.

The present invention is also directed to a method of producing Form I celecoxib wherein the method comprises milling or grinding a celecoxib solvate. A useful milling step can include for example, wet milling or ball milling. A useful grinding step can include for example, grinding or shaking.

Another embodiment of the present invention is a method of producing Form II celecoxib wherein the method comprises melting Form I celecoxib and cooling the melt thereby producing Form II celecoxib.

Another embodiment of the present invention is a method of producing Form II celecoxib wherein the method comprises melting Form III celecoxib and cooling the melt thereby producing Form II celecoxib.

Form III celecoxib is produced by crystallization of celecoxib from a solvent comprising isopropanol and water (see for example U.S. Pat. No. 5,910,597).

Form III celecoxib has a complex differential scanning calorimetry melting transition. When scanned at 0.5° C./min, the melting of Form III celecoxib is observed at about 160.8° C. followed by recrystallization to Form II celecoxib and subsequent melting of Form II at about 162.0° C. Form III celecoxib is the thermodynamically stable form of celecoxib.

Characterization of Polymorphic Crystalline Forms of Celecoxib

X-Ray Powder Diffraction (PXRD), Infrared Absorption Spectroscopy (IR), and Differential Scanning Calorimetry (DSC), as well as Raman Spectroscopy were used to characterize Forms I and Forms II.

X-Ray Powder Diffraction (PXRD)

The various crystalline forms of celecoxib can be analyzed with either a Siemens D5000 Powder Diffractometer or an Inel Multipurpose Diffractometer. For the Siemens D5000 Powder Diffractometer, the raw data can be measured for 2-theta values from 2° to 50°, with steps of 0.02° and step periods of two seconds. For the Inel Multipurpose Diffractometer, samples were placed in an aluminum sample holder and raw data was collected for 30 minutes at all two theta values simultaneously.

Figure 1:
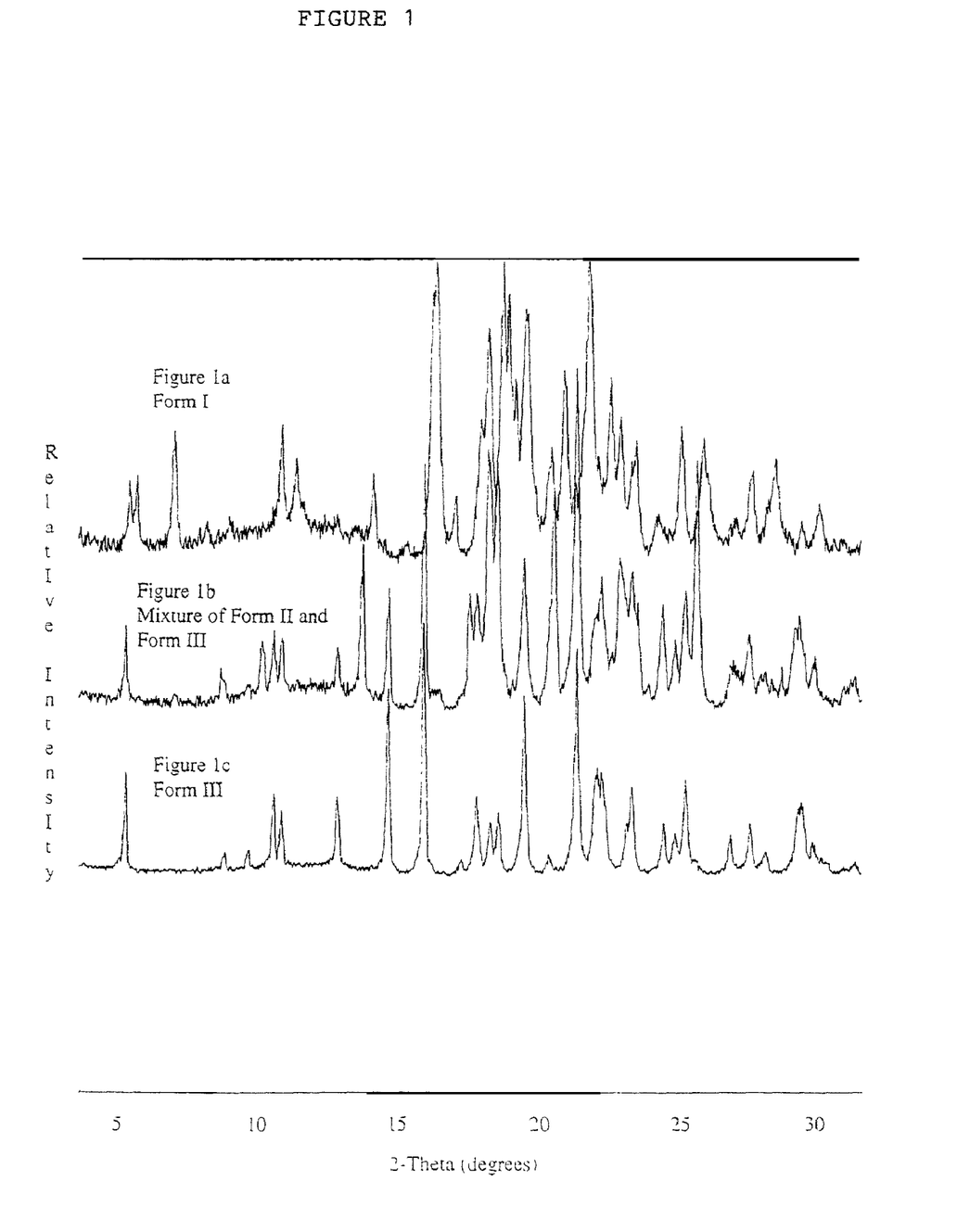
FIG. 1 depicts a comparison of experimental PXRD patterns between Form I celecoxib (FIG. 1a), a mixture of Form II celecoxcib and Form III celecoxib (FIG. 1b), and Form III celecoxib (FIG. 1c).

As illustrated in FIG. 1, the three forms were easily distinguishable by PXRD. Using a Cu x-ray source (1.54 nm), the characteristic diffractions were observed at 2-theta values of about 5.5°, 5.7°, 7.2° and 16.6° for Form I celecoxib and about 10.3°, 13.8° and 17.7° for Form II celecoxib.

Melting/Decomposition Temperature

The temperatures of melting and/or decomposition of non-solvated celecoxib crystalline forms were determined using a TA Instruments 2920 differential scanning calorimeter. Each sample (1-2 mg) was placed in either a sealed or unsealed aluminum pan and heated at 0.5° C./minute. Melting/decomposition ranges were defined from the extrapolated onset to the maximum of the melting/decomposition endotherm.

Three polymorphic forms of celecoxib have been identified. Polymorphic Form I celecoxib melted at about 162.8° C.; Form II celecoxib melted at about 161.5° C.; and Form III celecoxib melted at about 160.8° C. On melting, Form III celecoxib has been observed to partially recrystallize to Form II celecoxib or Form I celecoxib.

Three polymorphic forms and solvates of N,N-dimethylacetamide (DMA) and N,N-dimethylformamide (DMF) were identified. The physical properties and distinguishing characteristics of the novel polymorphs are shown in Table 1.

TABLE 1

| Form | Melting Point (° C.) | ΔH (J/g) | Distinguishing Transitions* | | |
|------|---------------------|----------|-----|-------|------------------|
| | | | IR | Raman | PXRD (2 theta) |
| I | 162.8 | 72 | 3356 cm$^{-1}$ 3356 cm$^{-1}$ | NA | 5.5°, 5.7°, 7.2° and 16.6° |
| II** | 161.5 | <84 | none | 712 cm$^{-1}$ | 10.3°, 13.8° and 17.7° |
| III | 160.8 | 91 | — | — | — |

*Characteristic transitions not observed for other forms.
**Pure samples of Form II celecoxib have not been produced.

Differential Scanning Calorimetry (DSC)

DSC is used to characterize the polymorphic forms of celecoxib. Form I celecoxib is the highest melting polymorph at 162.8° C. with an endotherm maximum at 163.3° C. Form II celecoxib melts at 161.5° C. and has an endotherm maximum at 162.0° C. A complex transition is observed for Form III celecoxib. The complexity of this transition, which is only observed at slow scan rates, represents melting of Form III celecoxib, followed by recrystallization to Form II celecoxib and subsequent melting of Form II celecoxib. Considering only the initial endothermic transition, Form III celecoxib melts at 160.8° C. and has an endotherm maximum at 161.5° C. DSC detects low levels of Form I celecoxib in Form III celecoxib.

Infrared Absorption Spectroscopy

Figure 2:
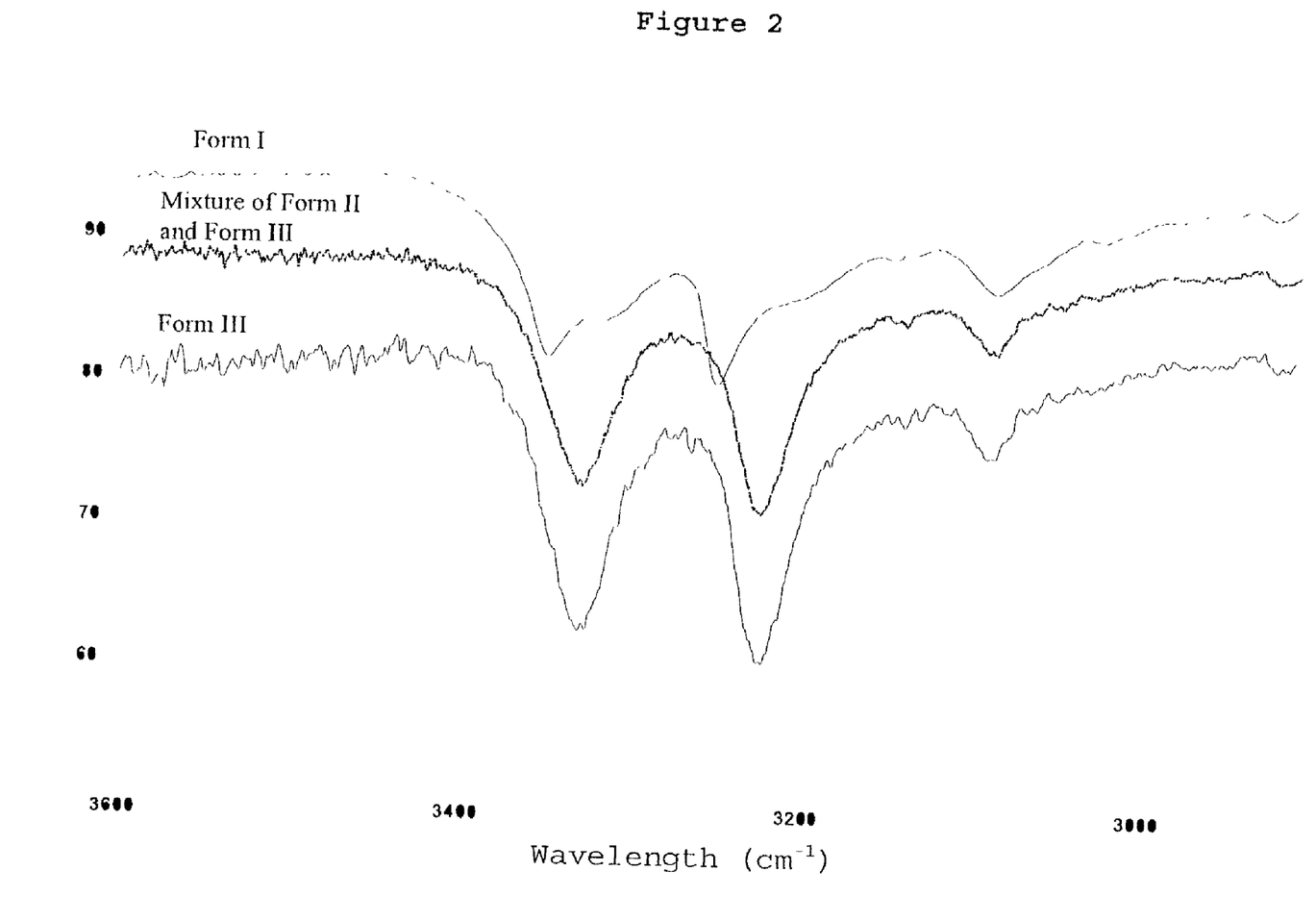
FIG. 2 depicts a comparison between the IR spectra of Form I celecoxib, a mixture of Form II celecoxcib and Form III celecoxib, and Form III celecoxib.
Figure 3:
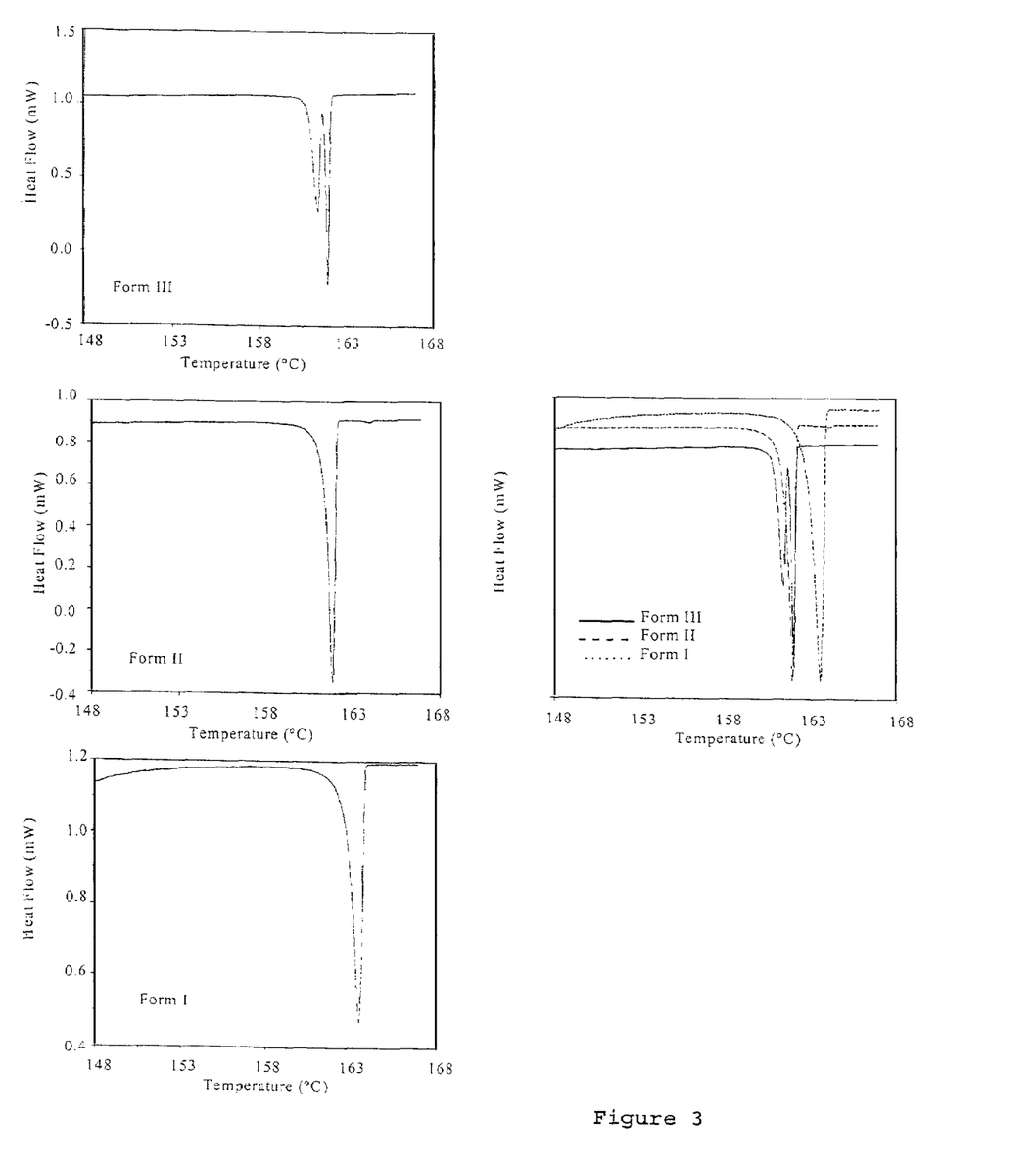
FIG. 3 depicts a comparison of DSC thermograms scanned at 0.5° C./minute for individual celecoxib Forms with overlay (endotherms down).

IR distinguished Form I celecoxib from Form II celecoxib and Form III celecoxib, (see FIG. 2).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

The following examples contain detailed descriptions of the methods of preparation of crystalline Form I and Form II celecoxib described in this application. These detailed descriptions fall within the scope, and serve to exemplify the invention. These detailed descriptions are presented for illustrative purposes only and are not intended as a restriction on the scope of the invention. All parts are by weight and temperatures are in degrees Centigrade unless otherwise indicated. The celecoxib starting material used in each of the following examples was prepared in accordance with U.S. Pat. No. 5,910,597.

PREPARATIVE EXAMPLES

Example 1

Preparation of a DMA Solvate of Celecoxib (a Ratio of 1:1 Celecoxib-DMA)

Method A. In a round bottom flask, 4.84 g of celecoxib were combined with approximately 125 mL of DMA. The solvent was removed at reduced pressure and at 60° C. to induce crystallization. The dry solids were collected on a filter. This process produced 5 g of 1:1 solvate. As determined by TGA at 10° C./min, decomposition began at about 100° C. with a maximum at about 148° C., and a total weight loss of 17%.

Method B. In a 1 L beaker, 38.2 g of celecoxib was placed in approximately 1000 mL of DMA with stirring. The resulting solution was transferred to a 2 L beaker. Approximately 400 mL of water was added to cause crystallization. The crystals were isolated by filtration. The wet yield was 5.44 g. Additional crystal crops were generated by the addition of water to the filtrate. TGA at 10° C./min showed decomposition beginning at about 100° C. with maximum at about 150° C., and with a total weight loss of 18% solvent.

Example 2

Preparation of a DMF Solvate of Celecoxib (a Ratio of 1:1 Celecoxib-DMF)

In a crystallizing dish, about 1 g of celecoxib was dissolved in 50 mL of DMF. The crystallizing dish, covered with aluminum foil, which was perforated with small holes, was placed in a hood and allowed to evaporate to dryness. This process produced about 1.02 g. TGA at 10° C./min showed two weight losses during decomposition which began at about 75° C. and continued with a second maximum at about 156° C. Total weight loss was 13.4%.

WORKING EXAMPLES

Example 1

General Methods for Preparing Celecoxib Form I

A. Preparation of Celecoxib Form I by Heating a Celecoxib Solvate:

An open container of a celecoxib solvate was heated in an oven at the lowest temperature at which desolvation was observed. Briefly, 0.3 g of celecoxibDMA was heated in an oven at about 100° C. for about 48 hours. The PXRD of the resulting sample showed characteristic reflections due to celecoxib Form I celecoxib as well as reflections of celecoxib-DMA; TGA showed a 9.6% weight loss centered at about 147° C., indicating about 50% conversion to Form I.

B. Preparation of Celecoxib Form I by Evaporation:

A high purity sample of celecoxib was crystallized from ethyl acetate-heptane solvent by evaporation. Celecoxib 16.03 g) was purified by preparative liquid chromatography using 15/85 (v/v)ethyl acetate/heptane and a 150 mm column (50.8 mm id) of 40-63 mcm silica gel. The fractions eluded between 270 mL and 900 mL were collected and combined. The solvent was removed at about 35° C. under vacuum to induce crystallization and evaporated to dryness. This process produced 8.6 g celecoxib Form I. Crystallizes were free of solvent, as determined by TGA, and had the Form I PXRD pattern shown in FIG. 1a.

C. Preparation of Celecoxib Form I by Melting:

In general, celecoxib was placed in an open container and was melted and then allowed to cool. In more detail, a beaker containing celecoxib was heated on a hot plate to 170° C. and the celecoxib was allowed to fully melt. Molten celecoxib was then poured on to a watch glass and allowed to cool. By DSC, scanned at 0.5° C./min, the melt of Form I was observed at about 163° C. The melt of Form III, and the recrystallization to Form II, and the melt of Form II, were also observed.

Example 2

General Methods for Preparing Celecoxib Form II

A. Preparation of Celecoxib Form II by Heating a Celecoxib Solvate:

1. Use of a DMA solvate.

In general, an open container of a celecoxib-DMA solvate was heated in an oven near the peak temperature at which desolvation was observed. Briefly, in an oven at about 130° C., 0.3 g of celecoxib-DMA was heated for approximately 48 hours. The PXRD of the resulting sample showed characteristic reflections due to celecoxib Form II as well as reflections of celecoxib Form III; DSC at 0.5° C./min showed a single melting endotherm with onset at 161.4° C. and maximum at 161.9° C.; TGA showed no weight loss below 200° C. The powder x-ray diffraction pattern of the mixture was shown in FIG. 1b.

2. Use of a DMF solvate.

In general, an open container of a celecoxib-DMF solvate was heated in an oven near the peak temperature at which desolvation was observed. Briefly, in an oven at about 130° C., approximately 0.2 g of celecoxib-DMF was heated overnight. The PXRD of the resulting sample showed characteristic reflections due to celecoxib Form II as well as reflections of celecoxib Form III; DSC at 0.5° C./min showed a one melting endotherm with onset at 161.5° C. and maximum at 161.8° C. and a small endothermic transition with maximum at about 163.8° C. (Form I); TGA showed no weight loss below 200° C.

B. Preparation of Celecoxib Form II from Celecoxib Form III, by Mechanical Conversion.

In general, celecoxib Form III was ground in a ball mill. Briefly, using a wiggle-bug, celecoxib Form III was ground at a maximum intensity for 30 seconds. The resulting solids were a mixture of Form III and Form II was determined by powder x-ray diffraction.

C. Preparation of Celecoxib Form II by Melting

Celecoxib was melted in a test tube at 170° C. using an oil bath. A Teflon spatula was dipped into the molten celecoxib, the spatula was removed, scraped, and the dried solids from the spatula were collected. The dried solids were a mixture of Form II and Form III as determined by powder x-ray. DSC at 10° C./min also showed the presence of Form I.

What is claimed is:

1. A Form I crystalline form of celecoxib having an X-ray powder diffraction pattern with peaks at about 5.5, 5.7, 7.2, or 16.6 degrees two theta when measured using a Cu X-ray source and having a melting range from about 160° C. to about 164° C.

2. The crystalline form of claim 1 having a melting range from about 162° C. to about 163° C.

3. The crystalline form of claim 2 having a melting point of about 162.8° C.

4. The crystalline form of claim 2 having a differential scanning calorimetry endotherm maximum from about 160.0° C. to about 164.0° C.

5. The crystalline form of claim 2 having an endotherm maximum at about 163.3° C.

6. The crystalline form of claim 5 further having a melting range from about 160° C. to about 164° C.

7. The crystalline form of claim 6 having a melting point of about 162.8° C.

8. The crystalline form of claim 1 having an Infrared Spectrum which has a peak at about 3250 to about 3260 $cm^{-1}$.

9. The crystalline form of claim 8 having an Infrared Spectrum which has a peak at about 3256 cm$^{-1}$.

10. The crystalline form of claim 1 having an Infrared Spectrum which has a peak at about 3350 to about 3360 cm$^{-1}$.

11. The crystalline form of claim 10 having an Infrared Spectrum which has a peak at about 3356 cm$^{-1}$.

12. The crystalline form of claim 1 having an Infrared Spectrum which has peaks at about 3256 cm$^{-1}$ and about 3356 cm$^{-1}$, and having a melting point of about 162.8° C.

13. The crystalline form of claim 1 having a phase purity of at least about 5% Form I celecoxib.

14. The crystalline form of claim 1 having a phase purity of at least about 10% Form I celecoxib.

15. The crystalline form of claim 1 having a phase purity of at least about 25% Form I celecoxib.

16. The crystalline form of claim 1 having a phase purity of at least about 50% Form I celecoxib.

17. The crystalline form of claim 1 having a phase purity of at least about 75% Form I celecoxib.

18. The crystalline form of claim 1 having a phase purity of at least about 90% Form I celecoxib.

19. The crystalline form of claim 1 having a substantially phase pure form of Form I celecoxib.

* * * * *